(12) United States Patent
Berry et al.

(10) Patent No.: US 7,622,112 B2
(45) Date of Patent: Nov. 24, 2009

(54) ANTI-SARS MONOCLONAL ANTIBODIES

(76) Inventors: Jody Berry, 1015 rue Arlington St. T2420, Winnipeg Manitoba (CA) R3E 3R2; Steven Jones, 1015 rue Arlington St. T2420, Winnipeg Manitoba (CA) R3E 3 R2; Xin Yong Yuan, 1015 rue Arlington St. T2420, Winnipeg Manitoba (CA) R3E 3R2; Mike Gubbins, 1015 rue Arlington St. T2420, Winnipeg Manitoba (CA) R3E 3R2; Anton Andonov, 1015 rue Arlington St. T2420, Winnipeg Manitoba (CA) R3E 3R2; Hana Weingartl, 1015 rue Arlington St. T2420, Winnipeg Manitoba (CA) R3E 3R2; Mike Drebot, 1015 rue Arlington St. T2420, Winnipeg Manitoba (CA) R3E 3R2; Frank Plummer, 1015 rue Arlington St. T2420, Winnipeg Manitoba (CA) R3E 3R2

( * ) Notice: Subject to any disclaimer, the term of this patent is extended or adjusted under 35 U.S.C. 154(b) by 23 days.

(21) Appl. No.: 10/581,613

(22) PCT Filed: Dec. 6, 2004

(86) PCT No.: PCT/CA2004/002084

§ 371 (c)(1),
(2), (4) Date: Feb. 19, 2007

(87) PCT Pub. No.: WO2005/054469

PCT Pub. Date: Jun. 16, 2005

(65) Prior Publication Data

US 2008/0081047 A1   Apr. 3, 2008

Related U.S. Application Data

(60) Provisional application No. 60/526,971, filed on Dec. 5, 2003, provisional application No. 60/568,225, filed on May 6, 2004.

(51) Int. Cl.
| | |
|---|---|
| A61K 39/42 | (2006.01) |
| C12N 15/09 | (2006.01) |
| C12N 15/13 | (2006.01) |
| C12P 21/08 | (2006.01) |
| C12P 21/00 | (2006.01) |
| C07K 16/10 | (2006.01) |
| C07K 16/46 | (2006.01) |

(52) U.S. Cl. .......... 424/133.1; 424/147.1; 435/440; 435/69.6; 435/69.7; 530/387.3; 530/388.3; 530/413; 536/23.4; 536/23.53

(58) Field of Classification Search .......... None
See application file for complete search history.

(56) References Cited

FOREIGN PATENT DOCUMENTS

| WO | 2005/027847 | 3/2004 |
| WO | 2004/092332 | 10/2004 |
| WO | 2004/092360 | 10/2004 |
| WO | 2005/010034 | 2/2005 |

OTHER PUBLICATIONS

Gubbins MJ et al "Molecular characterization of a panel of murine monoclonal antibodies specific for the SARS-coronavirus" Molecular Immunology vol. 42, Aug. 9, 2004 pp. 125-136.
Berry JD et al "Development and characterization of neutralising monoclonal antibody to the SARS-coronavirus" Journal of Virological Methods vol. 120 No. 1. Sep. 1, 2004 pp. 87-96.
Sui J. et al "Potent neutralization of Severe Acute Respiratory Syndrome (SARS) coronavirus by a human MAb to S1 protein that blocks receptor association" Proceedings of the National Academy of Sciences vol. 101, No. 8 Feb. 24, 2004 pp. 2536-2541.
Zhou et al "An exposed domain in the Severe Acute Respiratory Syndrome coronavirus spike protein induces neutralizing antibodies" Journal of Virology vol. 78 No. 13 Jul. 2004 pp. 7217-7226.
Che Xy et al "Rapid and efficient preparation of monoclonal antibodies against SARS associated coronavirus nucleocapsid protein by immunizing mice" Di YiJun Yi Da Xue Xue Bao vol. 23 No. 7 Jul. 2003 pp. 640-642.
He Y et al "Receptor binding domain of SARS CoV spike protein induces highly potent neutralizing antibodies: implicated for developing subunit vaccine" Biochemical and Biophysical Research Communications vol. 324, Oct. 2, 2004 pp. 773-781.
Xiong S et al "immunogenicity of SARS inactivated vaccine in BALB/c mice " Immunology Letters vol. 95, Aug. 1, 2004 pp. 139-143.
Holmes K: :SARS coronavirus: a new challenge for prevention and therapy: The Journal of Clinicla Investigation vol. 111, Jun. 1, 2003 pp. 1605-1609.
Rota PA et al "Characterization of a novel coronavirus associat ed with severe acute respiratory syndrome "Science vol. 300 May 30, 2003 pp. 1394-1399.

*Primary Examiner*—Mary E Mosher
(74) *Attorney, Agent, or Firm*—Michael R. Williams; Ade & Company Inc.

(57) ABSTRACT

Monoclonal antibody reagents that recognize the SARS-coronavirus (SARS-HCoV) are needed urgently. In this report we describe the development and immunochemical characterization of mAbs against the SARS-HCoV based upon their specificity, binding requirements, and biological activity. Initial screening by ELISA, using highly purified virus as the coating antigen, resulted in the selection of seventeen mAbs. Five mAbs exhibited Western immunoblot reactivity with the denatured spike protein, of which two demonstrated the ability to neutralize SARS-HCoV in vitro. Another four Western immunoblot-negative mAbs also neutralize the virus. These antibodies will be useful for the development of diagnostic tests, pathogenicity and vaccine studies.

9 Claims, 16 Drawing Sheets

Figure 1

Figure 2:
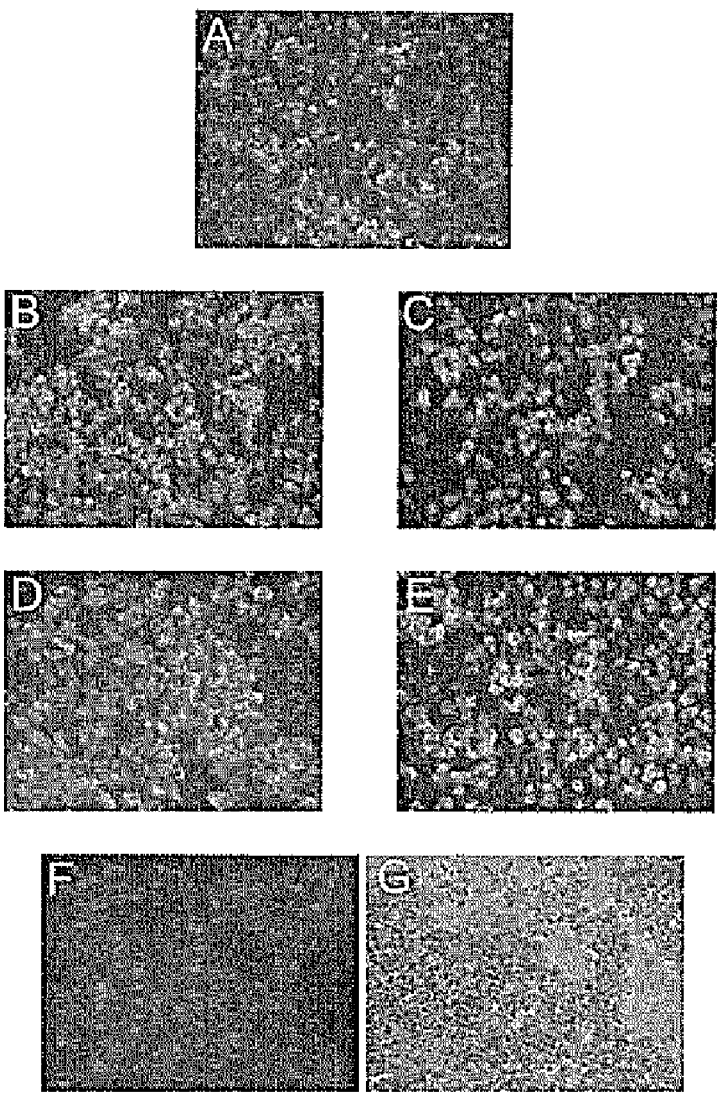
Figure 3:
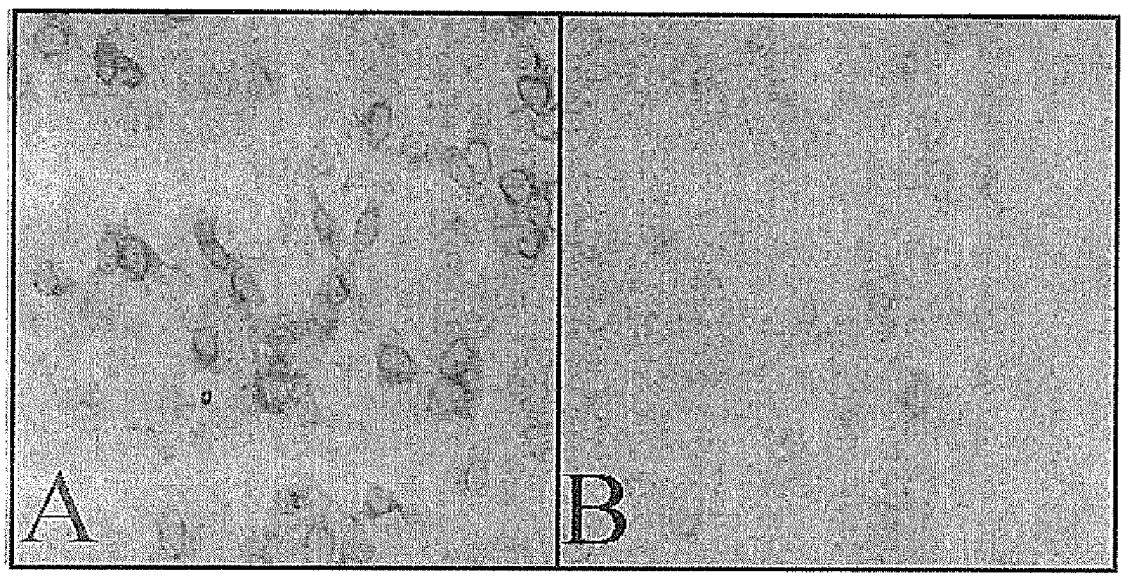
Figure 4:
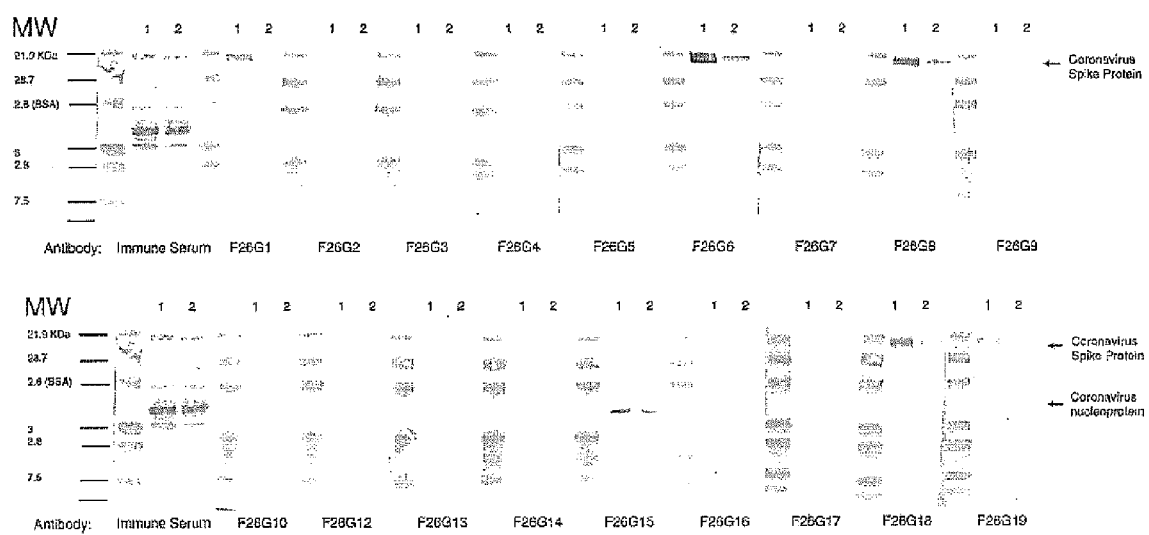

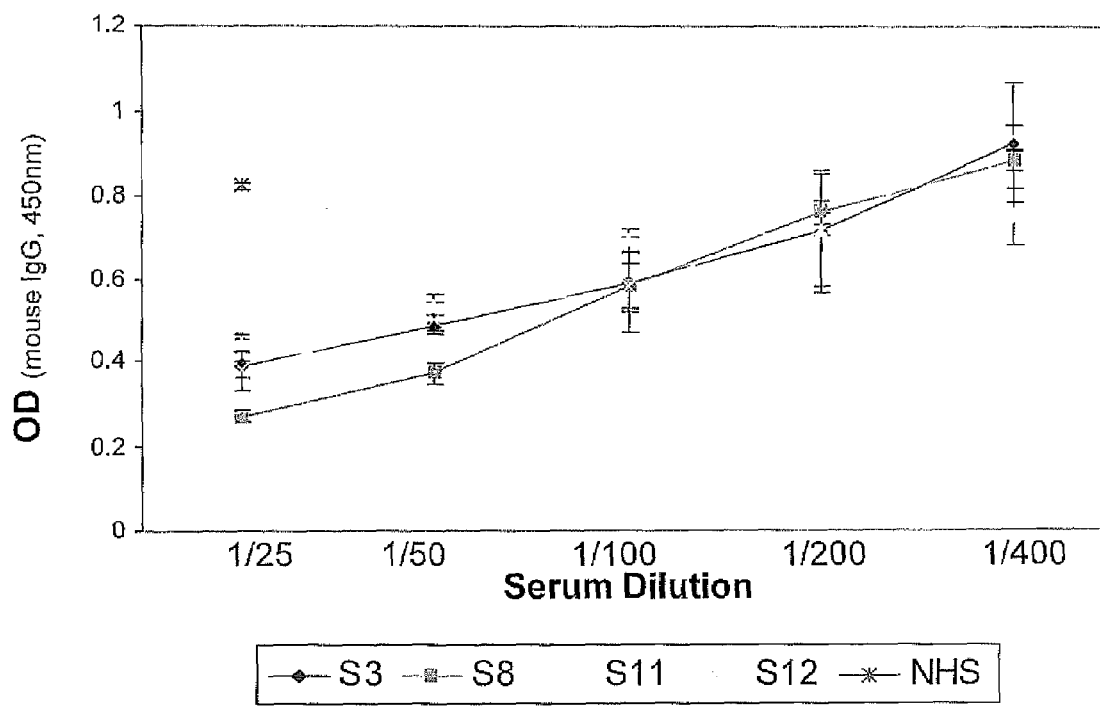
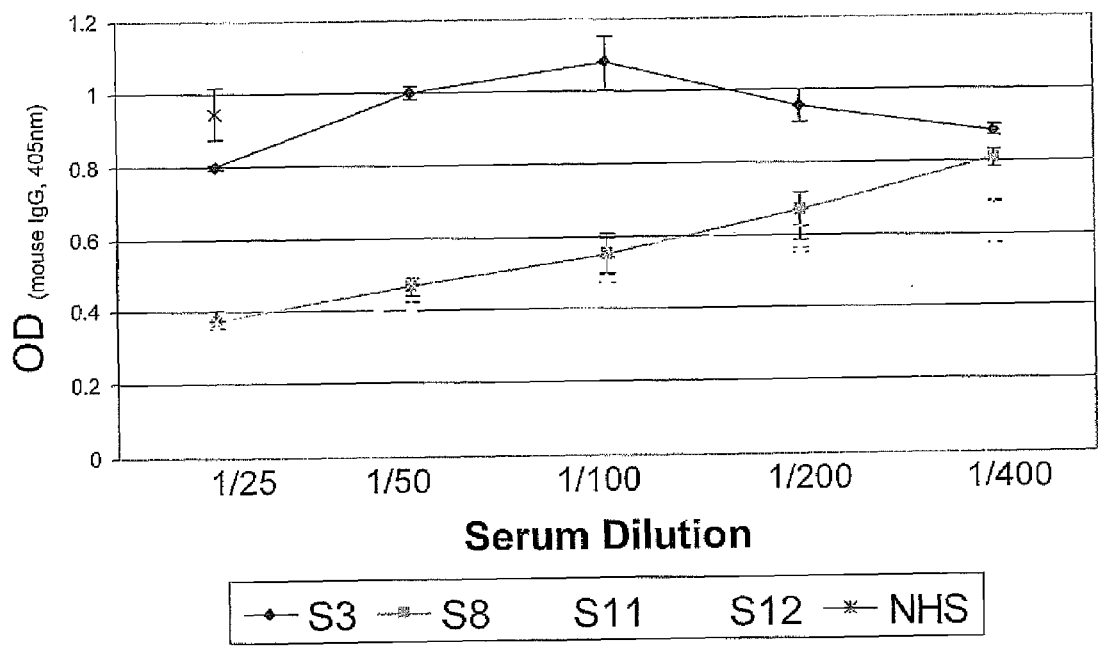
Figure 5

Figure 6A

SARS CoV mAb V$_H$ alignment

```
               FR 1           CDR1    FR 2  CDR2              FR 3                          CDR3
            *         20         *         40         *         60         *         80         *        100         *        120
G1_heavy  : EVQLEESGPGLVAPSQSLSITCTVSGFSLTNYDISWIRQPPGKGLEWLGIIWTG-GGTSYNSAFHSRLSISKDNSKSQVFLKMNSLQTDDTAIYYCVRDR---VYYFPMDYWGQGTSVTVSSAKTTAPS  : 125
G3_heavy  : EVRLQQSGPELVKPGASVKISCKTSGYTFTEYTMHWVKQSHGKNLEWIGGINPNNGGTTYNQKFKGKATLTVDKSSNTAYMELRSLTSEDSAVYYCSRGDYGTSYGYFDVWGAGTTVTVSSAKTTAPSV : 129
G6_heavy  : QVQLQQPGAELVKPGASVKLSCKASGYTFTNYWIHWVKQRPGQGLEWIGEINPGNGRTNYNGNFMNKATLTVDKSSNTAYMQLSSLTSEDSAVYHCAR------LDYWGQGTTLTVSSAKTTPPS    : 119
G15_heavy : EVQLQQSGPELVKPGVSHKISCKASGYSFTGYTMNWVKQSHGKNLEWIGLINPYNGGTNYNQKFKGKATLTVDKSSSTAYNELLSLTSEDSAVYYCARSYYGSSPYYAMDYWGQGTSVTVSSAKTTAPS  : 129
G18_heavy : LVQLEESGTVLPRPGASVKMSCKASGYTTTSYWMHWVKQRPGQGLEWIGALIYPGWSDTNYNQKFTNYNQKGRAILTAVTSTSTASMELSSLTNEDSAVYYCTRDGYGSLYYYAMDFWGQGTSVTVSSAKTTAPS : 129
```

Figure 6B

SARS-specific monoclonal antibodies, Heavy chains (VH), amino acid sequences

F26G3-VH
EVRLQQSGPELVKPGASVKISCKTSGYTFTEYTMHWVKQSHGKNLEWIGGINPNNGGTTYNQKFKG
KATLTVDKSSNTAYMELRSLTSEDSAVYYCSRGDYGTSYGYFDVWGAGTTVTVSSAKTTAPSVYPL
A

F26G7-VH

VELLESGTVLARPGASVKMSCEASGYTFTTYWMHWIKQRPGQGLEWIGAIYPGNSDTTYNQKFKGK
AKLTAVTSTSTAYMELSSLTNEDSAVYYCTREGIPQLLRTMDYWGQGTSVTVSSAKTTPPSV

F26G9-VH

VQLLESGTVLARPGASVKMSCKASGYSFTSYWMHWVKQRPGQGLEWIGAIYPGNSDTSYNQKFKGK
AKLTAVTSASTAYMELSSLTNEDSAVYYCTRSVYYGYGYFDVWGAGTTVTVSSAKTTPPSV

F26G10-VH

EVQLEESGTVLARPGASVKMSCKASGYSFTSYWMHWVKQRPGQGLDWIGAIYPENSDTSYNQKFKG
KAKLTAVTSASTAYMEHSSLTNEDSAVYYCTRSVYYGYGYFDVWGAGTTVTVSSAKTTAPSVYPLA
PVCGDTTGSSVTLGCLVKGYFPEPVTLTWNSGSLSSGVHTFPAVLQSDLYTLSSSVTVTSSTWPSQ
SITCNVAHPASSTKVDKKIEPRVPTSQN

F26G18-VH

LVQLEESGTVLPRPGASVKMSCKASGYTFTSYWMHWVKQRPGQGLEWIGAIYPGNSDTNYNQKFKG
RATLTAVTSTSTASMELSSLTNEDSAVYYCTRDGYGSLYYYAMDFWGQGTSVTVSSAKTTAPSVK

F26G19-VH

EVQLEESGTVLARPGASVKMSCKASGYTFTTYRMHWIKQRPGQGLEWIGAIYPGNSDTTYNQKFKD
KAKLTAVTSTSSAYMELSSLTNEDSAVYFCTREGIPQLLRTLDYWGQGTSVTVSSAKTTAPSVYPL
A

F26G1-VH

EVQLEESGPGLVAPSQSLSITCTVSGFSLTNYDISWIRQPPGKGLEWLGIIWTGGGTSYNSAFMSR
LSISKDNSKSQVFLKMNSLQTDDTAIYYCVRDRVYYFPMDYWGQGTSVTVSSAKTTAPSVYPLA

F26G6-VH

MEWSWVFLFLVATATDVHSQVQLQQPGAELVKPGASVKVSCKASGYTFTNYWIHWVKQRPGQGLEW
IGEINPGNGRTNYNGNFMNKATLTVDKSSNTAYMQLSSLTSEDSAVYHCARLDYWGQGTTLTVSSA
KTTPPSV

F26G8-VH

VQLLESGAELVKPGASVKVSCKASGYTFTSYWIHWVKQRPGQGLEWIGEINPSNGRTNYNGNFESK
ATLTVDKSSNTAYMHLSSLTYEDSAVYHCTRLDYWGQGTTLTVSSAKTTAPSVYPLA

Neutralizing mAbs are in bold text.

FIGURE 7

SARS-specific monoclonal antibodies, Light chains (VL), amino acid sequences

F26G3-VL
DILMTQSPTSFAVSLGQRATISCRTSQSVSTSSYSYMHWYQQKPGQPPKLLIKYASNLESGVPARF
SGSGSGSDFTLNIHPVEEGDTATYYCQHSWEIPCAFGGGTKLEIKRADAAPTVS

F26G7-VL
ELVMTQSPSSLSASLGERVSLTCRASQEISGYLSWLQQKPDGTIKRLIYAASTLDSGVPKRFSGSR
SGSDYSLTISSLESEDFADYYCLQYISYPWTFGGGTKLEIKRADAAPTVS

F26G9-VL
DILMTQSHKCMSTSVGDRVSITCKASQDVSTAVVWYQQKPGQFPKLLIYWASTRHTGVPDRFTGSG
SGTDYTLTISSVQAEDLALYYCQQHYTTPYTFGGGTKLEIKRADAAPTVS

F26G10-VL
DILMTQSHKFMSTSVGDRVSITCKASQDVSTAVAWYQQKPGQSPKLLIYWASTRHTGVPDRFTGSG
SGTDYTLTISSVQAEDLALYYCQQHYSTPYTFGGGTKLEIKRADAAPTVS

F26G18-VL
ELVMTQSPSSLSASLGDRVTISCRASQDISNYLNWYQQKPDGTVKLLIYYTSRLHAGVPSRFSGSG
SGTDYSLTISNLEQEDIATYFCQQGYTLPYTFGGGTKLEIKRADAAPTVSKGEFQHTGGRY

F26G19-VL
DILMTQSPSSLSASLGERVSLTCRASQEISGYLSWLQEKPDGTIKRLIYAASTLDSGVPKRFSGSR
SGSDYSLTISSLESEDFADYYCLQYVSYPWTFGGGTKLEIKRADAAPTV

F26G1-VL
ELVMTQSPVSITASRGEKVTITCRASSSISSNYLHWYQQKPGSSPKLLIYRTSILASGVLDTFSGS
GSESSYTLTISCMQDEVAATYYCQQGSSSPPHVRRGDQAGNKTG

F26G6-VL
ELVMTQSPASLSVATGKKVTIRCISSTDIDDDMNWYQQKAGKPPKLLISEGNIFSPGVPSRFSSSG
NGTDFVFTVENTLSEDVADNYCLQSDNMPFTFGSGTKLGIKRADAAPTVS

F26G8-VL
ELVMTQSPASLSVITGKKVTIRCISNTDIDDDLNWSQLKAGEPPKLLISEGNIFSPGVPSRFSSSG
NGTDFVFTIENTLSEDVANNYCFQSDNMPFTFGSGTKLEIKRADAAPTVS

Neutralizing mAbs are in bold text.

FIGURE 8

SARS-specific monoclonal antibodies, Heavy chains (VH), nucleotide sequences

F26G3-VH
ATGGAATGGAGCTGGGTCTTTCTCTTTCTCCTGTCAGGAACTGCAGGTGTCCTCTCTGAGGTCCGG
CTGCAACAGTCTGGACCTGAACTGGTGAAGCCTGGGGCTTCAGTGAAGATATCCTGCAAGACTTCT
GGATACACATTCACTGAATACACCATGCACTGGGTGAAGCAGAGCCATGGAAAGAACCTTGAGTGG
ATTGGAGGTATTAATCCTAATAATGGTGGTACTACCTACAACCAGAAGTTTAAGGGCAAGGCCACA
TTGACTGTAGACAAGTCCTCCAACACAGCCTACATGGAGCTCCGCAGCCTGACATCTGAGGATTCT
GCAGTCTATTATTGTTCAAGAGGGGACTACGGTACTAGCTACGGGTACTTCGATGTCTGGGGCGCA
GGGACCACGGTCACCGTCTCCTCAGCCAAAACAACAGCCCCATCGGTCTATCCACTGGCCA

F26G7-VH

GTGGAGCTGCTCGAGTCAGGGACTGTGCTGGCAAGGCCTGGGGCTTCAGTGAAGATGTCCTGCGAG
GCTTCTGGCTACACCTTTACCACCTACTGGATGCACTGGATAAAACAGAGGCCTGGACAGGGTCTG
GAATGGATTGGCGCTATTTATCCAGGAAATAGTGATACTACCTACAACCAGAAGTTCAAGGGCAAG
GCCAAACTGACTGCAGTCACATCCACCAGCACTGCCTACATGGAGCTCAGCAGCCTGACAAATGAG
GACTCTGCGGTCTATTACTGTACAAGAGAGGGAATTCCCCAATTACTTCGGACTATGGACTACTGG
GGTCAAGGGACCTCAGTCACCGTCTCCTCAGCCAAAACAACACCCCCATCGGTCA

F26G9-VH

GTCCAGCTGCTCGAGTCTGGGACTGTGCTGGCAAGGCCTGGGGCTTCCGTGAAGATGTCCTGCAAG
GCTTCTGGCTACAGCTTTACCAGCTACTGGATGCACTGGGTAAAACAGAGGCCTGGACAGGGTCTA
GAATGGATTGGTGCTATTTATCCTGGAAATAGTGATACTAGCTACAACCAGAAGTTCAAGGGCAAG
GCCAAACTGACTGCAGTCACATCCGCCAGTACTGCCTACATGGAGCTCAGCAGCCTGACAAATGAG
GACTCTGCGGTCTATTACTGTACAAGATCCGTTTACTACGGCTACGGGTACTTCGATGTCTGGGGC
GCAGGGACCACGGTCACCGTCTCCTCAGCCAAAACAACACCCCCATCGGTC

F26G10-VH

GAGGTGCAGCTGGAGGAGTCTGGGACTGTGCTGGCAAGGCCTGGGGCTTCCGTGAAGATGTCCTGC
AAGGCTTCTGGCTACAGCTTTACCAGCTACTGGATGCACTGGGTAAAACAGAGGCCTGGACAGGGT
CTAGATTGGATTGGTGCTATTTATCCTGAAAATAGTGATACTAGCTACAACCAGAAGTTCAAGGGC
AAGGCCAAACTGACTGCAGTCACATCCGCCAGCACTGCCTACATGGAGCACAGCAGCCTGACAAAT
GAGGACTCTGCGGTCTATTACTGTACAAGATCCGTTTACTACGGCTACGGGTACTTCGATGTCTGG
GGCGCAGGGACCACGGTCACCGTCTCCTCAGCCAAGACAACAGCCCCATCGGTCTATCCACTGGCC
CCTGTGTGTGGAGATACAACTGGCTCCTCGGTGACTCTAGGATGCCTGGTCAAGGGTTATTTCCCT
GAGCCAGTGACCTTGACCTGGAACTCTGGATCCCTGTCCAGTGGTGTGCACACCTTCCCAGCTGTC
CTGCAGTCTGACCTCTACACCCTCAGCAGCTCAGTGACTGTAACCTCGAGCACCTGGCCCAGCCAG
TCCATCACCTGCAATGTGGCCCACCCGGCAAGCAGCACCAAGGTGGACAAGAAAATTGAGCCCAGA
GTGCCCACTAGTCAGAAC

F26G18-VH

TTGGTGCAGCTGGAGGAGTCTGGGACTGTGTTGCCAAGGCCTGGGGCTTCAGTGAAGATGTCCTGC
AAGGCTTCTGGCTACACCTTTACCAGCTACTGGATGCACTGGGTAAAACAGAGGCCTGGACAGGGT
CTGGAATGGATTGGCGCTATTTATCCTGGAAATAGTGATACTAACTACAACCAGAAGTTCAAGGGC
AGGGCCACACTGACTGCAGTCACATCCACCAGCACTGCCTCCATGGAGCTCAGCAGCCTGACAAAT
GAGGACTCTGCGGTCTATTACTGTACAAGAGACGGCTATGGTAGCCTTTATTACTATGCTATGGAC
TTCTGGGGTCAAGGAACCTCAGTCACCGTCTCCTCAGCCAAAACAACAGCCCCATCGGTCAAGGGC
GA

FIGURE 9 -1

F26G19-VH
GAGGTGCAGCTGGAGGAGTCTGGGACTGTGCTGGCAAGGCCTGGGGCTTCAGTGAAGATGTCCTGC
AAGGCTTCTGGCTACACCTTTACCACCTACCGGATGCACTGGATAAAACAGAGGCCTGGACAGGGT
CTGGAATGGATTGGCGCTATTTATCCTGGAAATAGTGATACTACCTACAACCAGAAGTTCAAGGAC
AAGGCCAAACTGACTGCAGTCACATCCACCAGCTCTGCCTACATGGAGCTCAGCAGCCTGACAAAT
GAGGACTCTGCGGTCTATTTCTGTACAAGAGAGGGAATTCCCCAATTACTTCGGACTTTGGACTAC
TGGGGTCAAGGAACCTCAGTCACCGTCTCCTCAGCCAAAACAACAGCCCCATCGGTCTATCCACTG
GCC

F26G1-VH
TGAGGTGCAGCTGGAGGAGTCAGGACCTGGCCTGGTGGCGCCCTCACAGAGCCTGTCCATTACCTG
CACTGTCTCTGGGTTCTCATTAACGAACTATGATATAAGCTGGATTCGCCAGCCACCAGGAAAGGG
TCTGGAGTGGCTTGGAATAATATGGACTGGTGGAGGCACAAGTTATAATTCAGCTTTCATGTCCAG
ACTGAGCATCAGCAAGGACAACTCCAAGAGCCAAGTTTTCTTAAAAATGAACAGTCTGCAAACTGA
TGACACAGCCATATATTACTGTGTAAGAGATAGGGTCTACTACTTCCCTATGGACTACTGGGGTCA
AGGAACCTCAGTCACCGTCTCCTCAGCCAAAACAACAGCCCCATCGGTCTATCCACTGGCCA

F26G6-VH
ATGGAATGGAGCTGGGTCTTTCTCTTTTTGGTAGCAACAGCTACAGATGTCCACTCCCAGGTCCAA
CTGCAGCAGCCTGGGGCTGAACTGGTGAAGCCTGGGGCTTCAGTGAAAGTGTCCTGCAAGGCTTCT
GGCTACACCTTCACCAACTACTGGATACACTGGGTGAAGCAGAGGCCTGGACAGGGCCTTGAGTGG
ATTGGAGAGATTAATCCTGGCAACGGTCGTACTAACTATAATGGGAACTTCATGAACAAGGCCACA
CTGACTGTAGACAAATCCTCCAACACAGCCTACATGCAACTCAGCAGCCTGACATCTGAGGACTCT
GCGGTCTATCACTGTGCAAGATTAGACTACTGGGGCCAAGGCACCACTCTCACAGTCTCCTCAGCC
AAAACAACACCCCCATCGGTC

F26G8-VH
GTCCAGCTGCTCGAGTCTGGGGCTGAACTGGTGAAGCCTGGGGCTTCAGTGAAAGTGTCCTGCAAG
GCTTCTGGCTACACCTTCACCAGCTACTGGATACACTGGGTGAAGCAGAGGCCTGGACAGGGCCTT
GAGTGGATTGGAGAGATTAATCCTAGCAACGGTCGTACTAACTATAATGGGAACTTCGAGAGCAAG
GCCACACTGACTGTAGACAAATCCTCCAACACAGCCTACATGCACCTCAGCAGCCTGACATATGAG
GACTCTGCGGTCTATCACTGTACAAGATTAGACTACTGGGGCCAAGGCACCACTCTCACAGTCTCC
TCAGCCAAAACAACAGCCCCATCGGTCTATCCACTGGCC

Neutralizing mAbs are in bold text.

FIGURE 9-2

SARS-specific monoclonal antibodies, Light chains (VL), nucleotide sequences

F26G3-VL
GGGCCCAGCCGGCCGAGCTCGACATTCTGATGACCCAGTCTCCTACTTCCTTTGCTGTATCTCTGG
GGCAGAGGGCCACCATCTCATGCAGGACCAGCCAAAGTGTCAGTACATCTAGCTATAGTTATATGC
ACTGGTACCAACAGAAACCAGGACAGCCACCCAAACTCCTCATCAAGTATGCATCCAACCTAGAAT
CTGGGGTCCCTGCCAGGTTCAGTGGCAGTGGGTCTGGGTCAGACTTCACCCTCAACATCCATCCTG
TGGAGGAGGGGGATACTGCAACATATTACTGTCAGCACAGTTGGGAGATTCCGTGCGCGTTCGGAG
GGGGGACCAAGCTGGAAATAAAACGGGCTGATGCTGCACCAACTGTATCC

F26G7-VL

GTGCCAGATGTGAGCTCGTGATGACCCAGTCTCCATCCTCCTTATCTGCCTCTCTGGGAGAAAGAG
TCAGTCTCACTTGTCGGGCAAGTCAGGAAATTAGTGGTTATTTAAGCTGGCTTCAGCAGAAACCAG
ATGGAACTATTAAACGCCTGATCTACGCCGCATCCACTTTAGATTCGGGTGTCCCAAAAAGGTTCA
GTGGCAGTAGGTCTGGGTCAGATTATTCTCTCACCATCAGCAGCCTTGAGTCTGAAGATTTTGCAG
ACTATTACTGTCTACAATATATTAGTTATCCGTGGACGTTCGGGGGAGGTACCAAGCTGGAAATCA
AACGGGCTGATGCTGCACCAACTGTATCC

F26G9-VL

GACATTCTGATGACCCAGTCTCACAAATGCATGTCCACATCAGTAGGAGACAGGGTCAGCATCACC
TGCAAGGCCAGTCAGGATGTGAGTACTGCTGTAGTCTGGTATCAACAAAAACCAGGGCAATTTCCT
AAACTACTGATTTACTGGGCATCCACCCGGCACACTGGAGTCCCTGATCGCTTCACAGGCAGTGGA
TCTGGGACAGATTATACTCTCACCATCAGCAGTGTGCAGGCTGAAGACCTGGCACTTTATTACTGT
CAGCAACATTATACCACTCCGTACACGTTCGGAGGGGGGACCAAGCTGGAAATAAAACGGGCTGAT
GCTGCACCAACTGTATCC

F26G10-VL

GGGCCCAGCCGGCCGAGCTCGACATTCTGATGACCCAGTCTCACAAATTCATGTCCACATCAGTAG
GAGACAGGGTCAGCATCACCTGCAAGGCCAGTCAGGATGTGAGTACTGCTGTAGCCTGGTATCAAC
AAAAACCAGGGCAATCTCCTAAACTACTGATTTACTGGGCATCCACCCGGCACACTGGAGTCCCTG
ATCGCTTCACAGGCAGTGGATCTGGGACAGATTATACTCTCACCATCAGCAGTGTGCAGGCTGAAG
ACCTGGCACTTTATTACTGTCAGCAACATTATAGCACTCCGTACACGTTCGGAGGGGGGACCAAGC
TGGAAATAAAACGGGCTGATGCTGCACCAACTGTATCC

F26G18-VL

GAGCTCGTGATGACCCAGTCTCCATCCTCCCTGTCTGCCTCTCTGGGAGACAGAGTCACCATCAGT
TGCAGGGCAAGTCAGGACATTAGCAATTATTTAAACTGGTATCAGCAGAAACCAGATGGAACTGTT
AAACTCCTGATCTATTACACATCAAGATTACACGCAGGAGTCCCATCAAGGTTCAGTGGCAGTGGG
TCTGGAACAGATTATTCTCTCACCATTAGCAACCTGGAGCAAGAAGATATTGCCACTTACTTTTGC
CAACAGGGTTATACGCTTCCGTACACGTTCGGAGGGGGGACCAAGCTGGAAATAAAACGGGCTGAT
GCTGCACCAACTGTATCCAA

F26G19-VL

GACATTCTGATGACCCAGTCTCCATCCTCCTTATCTGCCTCTCTGGGAGAAAGAGTCAGTCTCACT
TGTCGGGCAAGTCAGGAAATTAGTGGTTACTTAAGCTGGCTTCAGGAGAAACCAGATGGAACTATT
AAACGCCTGATCTACGCCGCTTCCACTTTAGATTCTGGTGTCCCAAAAAGGTTCAGTGGCAGTAGG
TCTGGGTCAGATTATTCTCTCACCATCAGCAGCCTTGAGTCTGAAGATTTTGCAGACTATTACTGT
CTACAATATGTTAGTTATCCGTGGACGTTCGGTGGAGGCACCAAGCTGGAAATCAAACGGGCTGAT
GCTGCACCAACTGTA

FIGURE 10-1

F26G1-VL
GTGCCAGATGTGAGCTCGTGATGACCCAGTCTCCAGTATCCATAACTGCATCTCGAGGGGAGAAGG
TCACCATCACCTGCCGTGCCAGCTCAAGTATAAGTTCCAATTACTTACACTGGTACCAGCAGAAGC
CAGGATCCTCCCCTAAACTTTTGATTTATAGGACATCCATCCTGGCATCTGGAGTCCTGGACACCT
TCAGTGGCAGTGGGTCTGAGAGCTCTTACACTCTGACAATCAGCTGCATGCAGGACGAAGTTGCTG
CCACTTACTATTGTCAGCAGGGGAGTAGTAGCCCACCACACGTTCGGAGGGGGGACCAAGCTGGAA
ATAAAACGGGCTGATGCTGCACCAACTGTATCCA

F26G6-VL
GTGCCAGATGTGAGCTCGTGATGACCCAGTCTCCAGCATCCCTGTCCGTGGCTACAGGAAAAAAAG
TCACCATCAGATGCATAAGCAGCACTGACATTGATGATGATATGAACTGGTACCAGCAGAAGGCAG
GAAAACCTCCTAAACTCCTTATTTCAGAAGGCAATATTTTTAGTCCTGGAGTCCCATCCCGATTCT
CCAGCAGTGGCAATGGCACAGATTTTGTTTTTACAGTTGAAAACACGCTCTCAGAAGATGTTGCAG
ATAACTACTGTTTGCAAAGTGATAACATGCCATTCACGTTCGGCTCGGGGACAAAGTTGGGAATAA
AACGGGCTGATGCTGCACCAACTGTATCC

F26G8-VL
GTGCCAGATGTGAGCTCGTGATGACCCAGTCTCCAGCATCCCTGTCCGTGATTACAGGAAAAAAAG
TCACCATCAGATGCATAAGCAACACTGACATTGATGATGATTTGAACTGGTCCCAGCTGAAGGCAG
GAGAACCTCCTAAACTCCTTATTTCAGAAGGCAATATTTTTAGTCCTGGAGTCCCATCCCGATTCT
CCAGCAGTGGCAATGGCACAGATTTTGTTTTTACAATTGAAAACACGCTCTCAGAAGATGTTGCAA
ATAACTACTGTTTCCAAAGTGATAACATGCCATTCACGTTCGGCTCGGGGACAAAGTTGGAAATAA
AACGGGCTGATGCTGCACCAACTGTATCC

Neutralizing mAbs are in bold text.

FIGURE 10-2

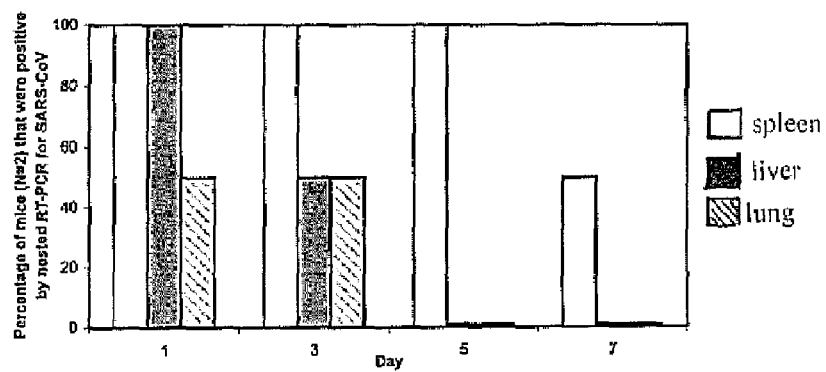
(A)
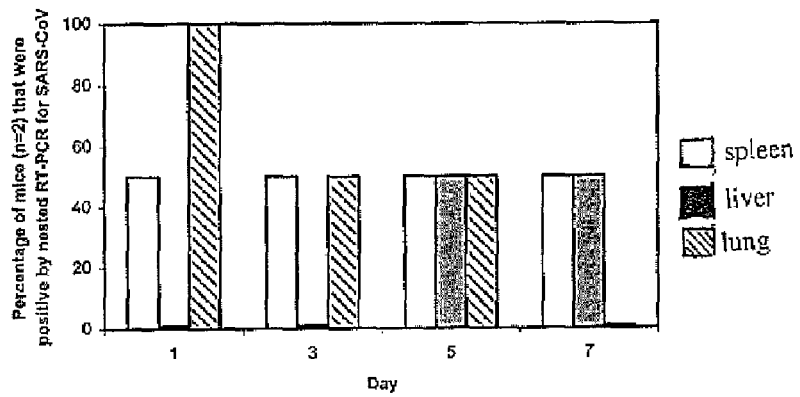
(B)
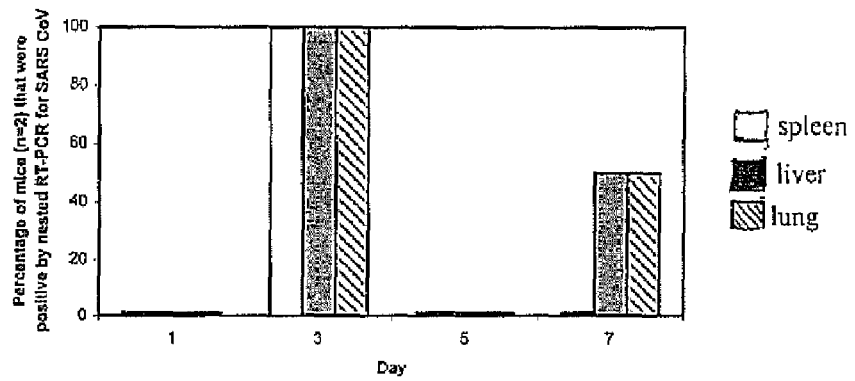
(C)
FIGURE 11

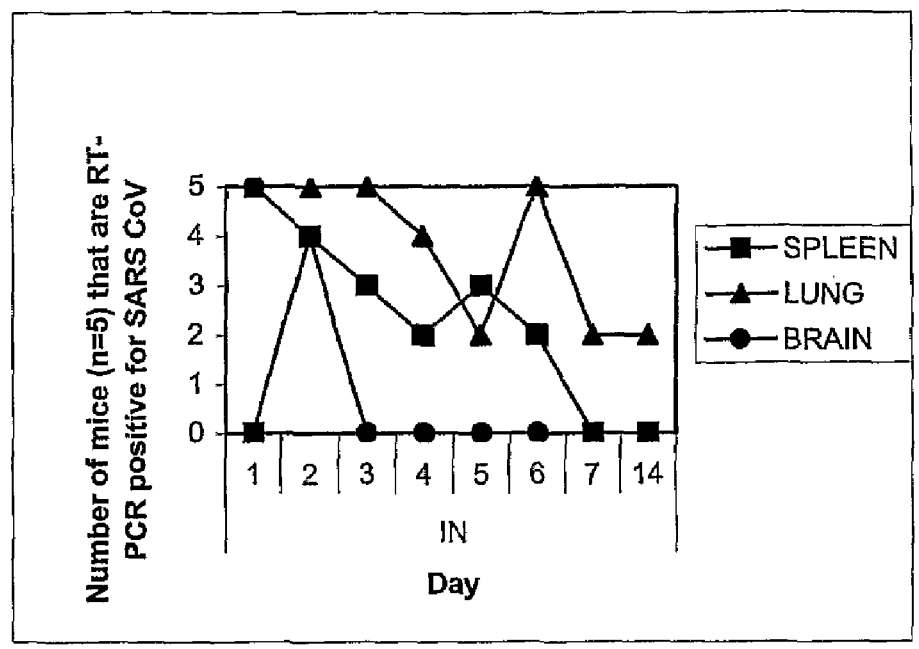
(A)
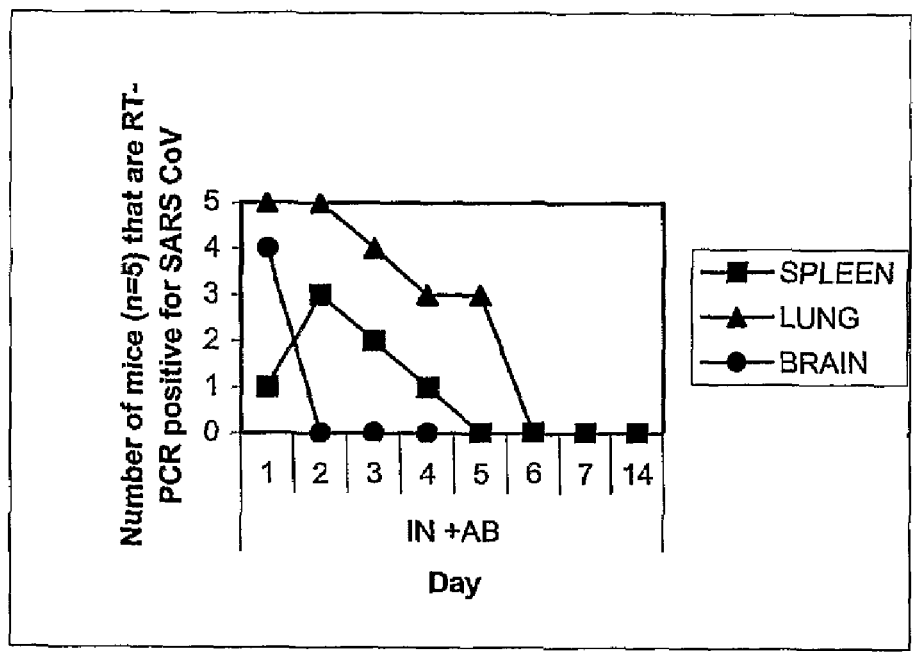
(B)
Figure 12

ANTI-SARS MONOCLONAL ANTIBODIES

The instant application is a 371 of PCT CA04/02084, filed Dec. 6, 2005, now abandoned, which claims the benefit of US Provisional Patent Application 60/526,971, filed Dec. 5, 2003, now abandoned, and US Provisional Patent Application 60/568,225, filed May 6, 2004, now abandoned.

FIELD OF THE INVENTION

The present invention relates generally to the field of therapeutic or medical treatments and methods of diagnosis and detection. More specifically, the present invention relates to a plurality of anti-SARS monoclonal antibodies.

BACKGROUND OF THE INVENTION

The SARS-Coronavirus (SARS-HCoV) has been implicated as the causative agent of SARS (severe acute respiratory syndrome) in humans. This virus has caused multiple deaths in various affected countries throughout the world. The SARS coronavirus spike protein has only 30% identity at the amino acid level to the spike proteins of the previously characterised coronaviruses. Recently, the genome of SARS isolates implicated in the 2003 Toronto outbreak were sequenced in their entirety (Marco et al., 2003, Science 300: 1399-1404; Rota et al., 2003, Science 300: 1394-1399). The production of mAbs specific to this agent is critical for diagnostic development, vaccine research and studies of viral pathogenesis. Assays that detect the presence of virally encoded proteins or nucleic acids may be preferable for diagnosis of SARS infections as the development of serum antibodies is quite protracted (Li et al., 2003, N. Engl. J. Med. 349: 508-509).

Coronaviruses acre enveloped, single stranded RNA viruses that replicate in the host cell cytoplasm [Fields, B. N., Knipe, D. M., Howley, P. M., and Griffin, D. E. (2001) Fields Virology (Lippincott Williams & Wilkins, Philadelphia, ed. 4)]. The coronaviruses form a single genus of the family Coronaviridae and the virions are large (80-160 nm in diameter), pleomorphic but generally spherical particles. Virions of most coronaviruses contain three major proteins: the phosphorylated nucleocapsid protein N; a small membrane-embedded glycoprotein (M); and a large club-shaped peplomer glycoprotein (S) which appears in EM micrographs as protruding spikes 20 nm in length. The M protein is synthesized on ribosomes bound to the endoplasmic reticulum and accumulates in the Golgi apparatus. The subcellular localization of M protein to the Golgi is believed to determine the site of virus budding from the infected cell. The S protein mediates many of the biological properties of the virus, including attachment to cell receptors, penetration, and cell-fusion, and it is the major target for virus-neutralizing antibodies (Collins et al., 1982, Virology 61:1814-1820; Talbot et al., 1984 Virology 132: 250-260; Wege and Dorrier, 1984, J. Gen. Virol. 65: 217-227; Laude et al., 1986, J. Gen. Virol. 67: 119-130; Jimenez et al., 1986, J. Virol. 60: 131-139; Godet et al., 1994, J. Virol. 68: 8008-8016). A proportion of the S glycoprotein that is not incorporated into budding virions is transported to the plasma membrane of the cell where it remains bound to the cell surface (Gerna et al., 1982, J. Gen. Virol. 60: 385-390).

Coronaviruses infect a wide range of mammalian hosts to produce a variety of disease outcomes including respiratory disease, enteritis and encephalitis. Antigenic similarities between various coronaviruses have been demonstrated to reside in the S protein and have been used to study evolution of this virus family [Brian, D. A., Hogue, B., Lapps, W., Potts, B. and Kapke, P. (1983) Proc. 4th Int. Symp. Neonatal Diarrhea (S.D. Acres, Saskatoon, Canada ed.)]. For most coronaviruses causing enteric and respiratory diseases the pathophysiological events leading to clinical symptoms are due to the acute cytocidal infection of the target cells. These infections can be limited by the local immune response resulting in the production of secretory antibodies specific for the S protein (Enjuanes et al., 1995, Dev. Biol. Stand. 84: 145-152). In contrast, many coronaviruses are maintained and spread in the population as inapparent and subclinical infections. The sequence of events leading to chronic disease is unknown but likely depends on the expression of viral genes, the functional impairment of host cells and the interaction with the host immune response.

There is a critical need to elucidate the immunologic basis for protection against SARS virus. The immunogenetics of antibody responses to protective epitopes is of particular importance and will lead to a clearer understanding of the nature of protective antibody responses to SARS. Lastly, the production of protective monoclonal antibodies may lead to the development of new recombinant therapeutic antibodies in order to provide rapid protection in SARS patients. In the present work we describe the development of murine mAbs against the SARS HCoV involved in the Toronto SARS outbreak. The mAbs were analysed for pertinent immunochemical properties and for their ability to neutralize the SARS virus in vitro.

SUMMARY OF THE INVENTION

According to a first aspect of the invention, there is provided a SARS detecting monoclonal antibody selected from the group consisting of: F26G1, F26G2, F26G4, F26G5, F26G6, F26G8, F26G12, F26G13, F26G14, F26G16, F26G17, F26G3, F26G7, F26G9, F26G10, G26G18 and F26G19.

According to a second aspect of the invention, there is provided a SARS neutralizing monoclonal antibody selected from the group consisting of F26G3, F26G7, F26G9, F26G10, F26G18 and F26G19.

According to a third aspect of the invention, there is provided a kit comprising at least one monoclonal antibody selected from the group consisting of: F26G1, F26G2, F26G4, F26G5, F26G6, F26G8, F26G12, F26G13, F26G14, F26G16, F26G17, F26G3, F26G7, F26G9, F26G10, G26G18 and F26G19.

According to a fourth aspect of the invention, there is provided a pharmaceutical composition comprising a SARS neutralizing monoclonal antibody selected from the group consisting of F26G3, F26G7, F26G9, F26G10, F26G18, F26G19 and combinations thereof and a suitable excipient.

According to a fifth aspect of the invention, there is provided a method of preparing a chimeric antibody comprising:

introducing an expression vector which comprises a nucleic acid encoding a constant region domain of a human light or heavy chain and a nucleic acid encoding a light chain variable region selected from the group consisting of G1-light (SEQ ID No. 1); G3-light (SEQ ID No. 2); G6-light (SEQ ID No. 3); G7-light (SEQ ID No. 4); G8-light (SEQ ID No. 5); G10-light (SEQ ID No. 6), G15-light (SEQ ID No. 7) and G18-light(SEQ ID No. 8) or a heavy chain variable region selected from the group consisting of G1-heavy (SEQ ID No. 9); G3-heavy (SEQ ID No. 10); G6-heavy (SEQ ID No. 11); G15-heavy (SEQ ID No. 12) and G18-heavy (SEQ ID No. 13) into a suitable host cell;

growing the host cell under conditions promoting expression of the chimeric antibody; and recovering the chimeric antibody.

According to a sixth aspect of the invention, there is provided a method of preparing a humanized antibody comprising:

providing a nucleic acid comprising a light chain variable region selected from the group consisting of G1-light (SEQ ID No. 1); G3-light (SEQ ID No. 2); G6-light (SEQ ID No. 3); G7-light (SEQ ID No. 4); G8-light (SEQ ID No. 5); G10-light (SEQ ID No. 6); G16-light (SEQ ID No. 7) and G18-light (SEQ ID No. 8) or a heavy chain variable region selected from the group consisting of G1-heavy (SEQ ID No. 9); G3-heavy (SEQ ID No. 10); G6-heavy (SEQ ID No. 11); G15-heavy (SEQ ID No. 12) and G18-heavy (SEQ ID No. 13);

modifying said nucleic acid such that at least one but fewer than about 30 of the amino acid residues of said variable region has been changed and/or deleted without disrupting antigen binding;

introducing said nucleic acid into a suitable host cell;

growing the host cell under conditions promoting expression of the humanized antibody; and recovering the humanized antibody.

According to a seventh aspect of the invention, there is provided a pharmaceutical composition comprising a chimeric antibody as described above and a suitable carrier.

According to an eighth aspect of the invention, there is provided a pharmaceutical composition comprising a humanized antibody described above and a suitable carrier.

According to a ninth aspect of the invention, there is provided a method of preparing a vaccine comprising:

recovering from a preparation of live, attenuated or recombinant SARS virus, antigens recognized by one or more Monoclonal antibodies selected from the group consisting of F26G1, F26G2, F26G4, F26G5, F26G6, F26G8, F26G12, F26G13, F26G14, F26G16, F26G17, F26G3, F26G7, F26G9, F26G10, G26G18 and F26G19.

According to a tenth aspect of the invention, there is provided a nucleic acid molecule encoding a peptide comprising a light chain variable region selected from the group consisting of G1-light (SEQ ID No. 1); G3-light (SEQ ID No. 2); G6-light (SEQ ID No. 3); G7-light (SEQ ID No. 4); G8-light (SEQ ID No. 5); G10-light (SEQ ID No. 6); G15-light (SEQ ID No. 7) and G18-light(SEQ ID No. 8) or a heavy chain variable region selected from the group consisting of G1-heavy (SEQ ID No. 9); G3-heavy (SEQ ID No. 10); G6-heavy (SEQ ID No. 11); G15-heavy (SEQ ID No. 12) and G18-heavy (SEQ ID No. 13).

BRIEF DESCRIPTION OF THE DRAWINGS

Figure 1:
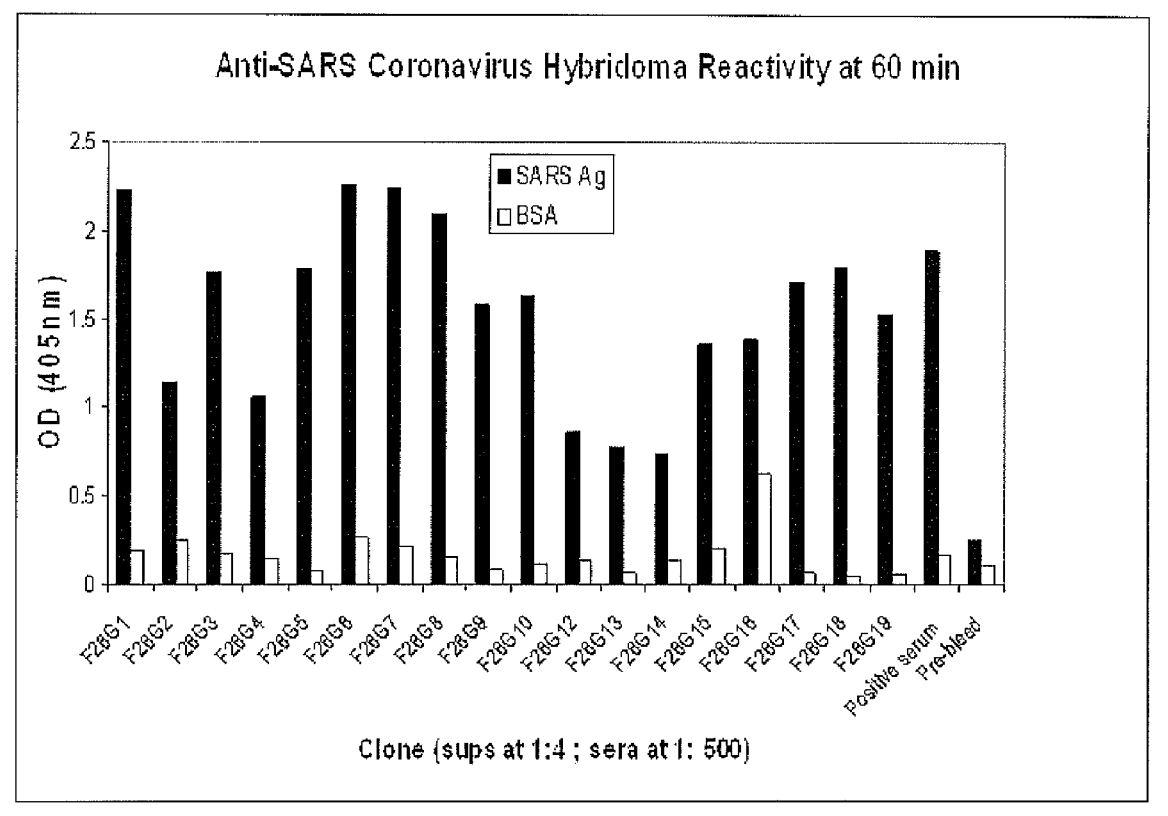

FIG. 1: ELISA results of monoclonal antibody on whole inactivated SARS virus and BSA. Hybridoma supernatants were tested at a ¼ dilution in PBS,0.2% BSA on pre-blocked plates, coated with 18 ng per well of inactivated virus. Positive clones were identified as having positive binding (color) in wells which were at least 4-fold higher than the background level reactivity on BSA. Antigen Legend: Black bars—native, purified SARS-HCov ; White bars—BSA (bovine serum albumin).

FIG. 2: Immunofluorescence staining of SARS HCOV-infected Vero cells with neutralizing and non-neutralizing SARS mAbs.; A. F26G6, non-neutralizing mab specific for the spike protein. B. F26G3, neutralizing mAb. C. F26G7, neutralizing mAb. D. F26G9, neutralizing mAb. E. Irrelevant mAb, F25G1. F. Irrelevant mAb F25G1 in bright field.

FIG. 3. Immunohistochemical analysis of binding of mAb F26G6 to (A) SARS infected but not (B) uninfected VERO cells.

FIG. 4. Western immunoblot of monoclonal antibody on whole inactivated SARS virus and infected vero cell lysates. The positive and preimmune control sera were from the corresponding immune mouse and tested at 1/2000 dilution in TBS, 0.2% BSA. Lanes marked 1 were loaded with purified virus; 2, with infected Vero cell lysate.

FIG. 5. This figure depicts Competion ELISA performed with F26G6 (anti0Spike) and F26G15 (anti-NP) mAbs on whole purified SARS virus as antigen. A dilution of each mAbs was shoosen that would produce approximately 50% maximum OD readin. Human normal and convalescent SARS-infected sera was diluted as shown at the bottom of the graph and used as a competitor for binding to the SARS antigen. A goat antimurine secondary antibody conjugated to HRP (preabsorbed with multiple species including human to remove any potential crossreactivity) was used to detect murine mAb binding. Abrogation or reduction of the signal indicates the presence of human antibody to the same antigen/epitope in the human human serum. This indicates that the individual was exposed or infected to the SARS corona virus. Our data also indicates that NP reactivity may be an earlier predictor of SARS infection as some sera inhibit NP bing mAb F26G15 but do not inhibit spike specific mAb F26G6. NHS=Normal human Sera tested at highest concentration 1/25; “S” are SARS patient convalescent sera.

Figure 6A:
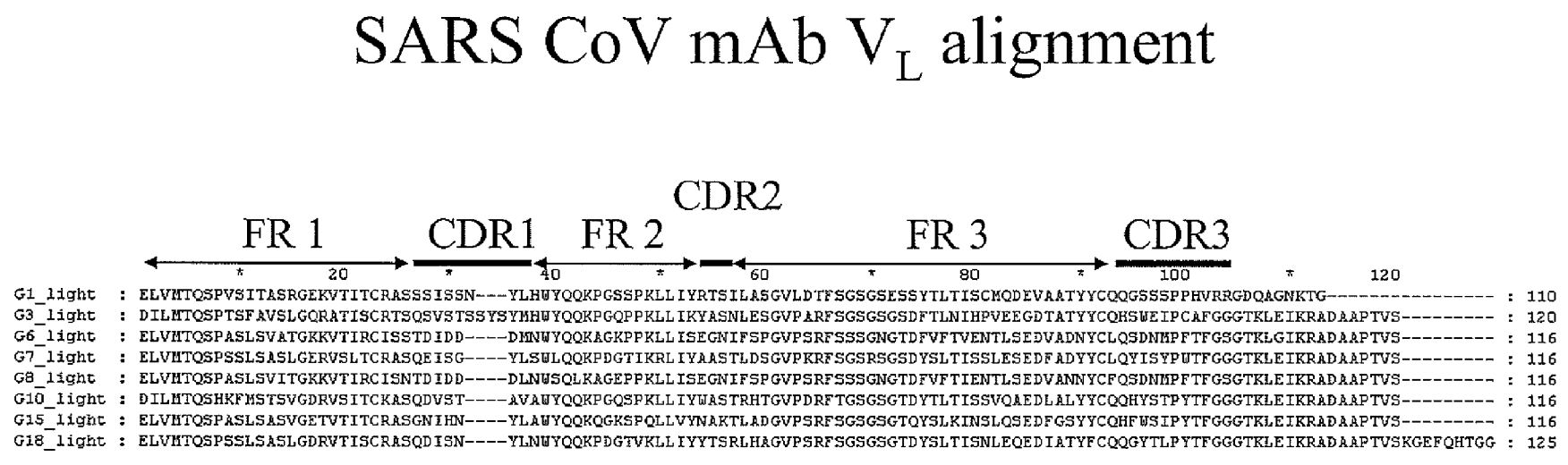

FIGS. 6A and 6B. Sequence data showing clones are unique and the id of the CDR regions that play a role in neutralization. FIG. 6A aligns G1-light (SEQ ID No. 16); G3-light (SEQ ID No. 10); G6-light (SEQ ID No. 17), G7-light (SEQ ID No. 11), G8-light (SEQ ID No. 18), G 10-light (SEQ ID No. 13), G15-light (SEQ ID No. 44) and G18-light (SEQ ID No. 14). FIG. 6B aligns G1-heavy (SEQ ID No. 7),G 3-heavy (SEQ ID No. 1), G6-heavy (SEQ ID No. 8), G15-heavy (SEQ ID No. 45) and G18-heavy (SEQ ID No. 5.. The data shows that none of the VH or VL genes of the anti-SARS neutralizing or Western immunoblot positive mAbs are the same. This means that each hybridoma was derived from a unique B cell and target SARS using different proteins. (i.e. not the same clone picked several times)

FIG. 7. SARS-specific monoclonal antibodies, Heavy chains (VH) amino acid sequences: F26G3-VH (SEQ ID No. 1); F26G7-VH (SEQ ID No. 2); F26G9-VH (SEQ ID No. 3); F26G10-VH (SEQ ID No. 4); F26G18 (SEQ ID No. 5); F26G19-VH (SEQ ID No. 6); F26G1-VH (SEQ ID No. 7); F26G6-VH (SEQ ID No. 8); and F26G8-VH (SEQ ID No. 9).

FIG. 8. SARS-specific monoclonal antibodies, Light chains (VL) amino acid sequences: F26G03-VL (SEQ ID No. 10); F26G7-VL (SEQ ID No. 11); F26G9-VL (SEQ ID No. 12); F26G10-VL (SEQ ID No. 13); F26G18-VL (SEQ ID No. 14); F26G19-VL (SEQ ID No. 15); F26G1-VL (SEQ ID No. 16); F26G6-VL (SEQ ID No. 17); and F26G8-VL (SEQ ID No. 18).

FIGS. 9-1 and 9-2. SARS-specific monoclonal antibodies, Heavy chains (VH) nucleotide sequences: F26G3-VH (SEQ ID No. 19); F26G7-VH (SEQ ID No. 20); F26G9-VH (SEQ ID No. 21); F26G10-VH (SEQ ID No. 22); F26G18-VH (SEQ ID No. 23); F26G19-VH (SEQ ID No. 24); F26G1-VH (SEQ ID No. 25); F26G6-VH (SEQ ID No. 26); and F26G8-VH (SEQ ID No. 27).

FIGS. 10-1 and 10-2. SARS-specific monoclonal antibodies, Light chains (VL) nucleotide sequences: F26G3-VL (SEQ ID No. 28); F26G7-VL (SEQ ID No. 29); F26G9-VL (SEQ ID No. 30); F26G10-VL (SEQ ID No. 31); F26G18-VL (SEQ ID No. 32); F26G19-VL (SEQ ID No. 33); F26G1-VL (SEQ ID No. 34); F26G6-VL (SEQ ID No. 35); and F26G8-VL (SEQ ID No. 36).

FIG. 11. Distribution of SARS CoV in spleen, liver and lung from mice infected via IP (A), IN (B) and OR (C). Organs were collected on days 1, 3, 5 and 7 p.i. and viral RNA was detected by nested RT-PCR using a primer set against the polymerase. Number of animals that were positive by RT-PCR is shown as a percentage (n=2).

FIG. 12. Number of mice that were RT-PCR positive in the spleen, lung and brain following IN inoculation of SARS CoV (A) or IP injection of neutralizing antibodies followed by IN inoculation of SARS CoV 2 hours later (B). N=5 per group and time point. Blood, liver and kidney have been omitted due to non-existent or insignificant levels of viral RNA.

Figure 13:
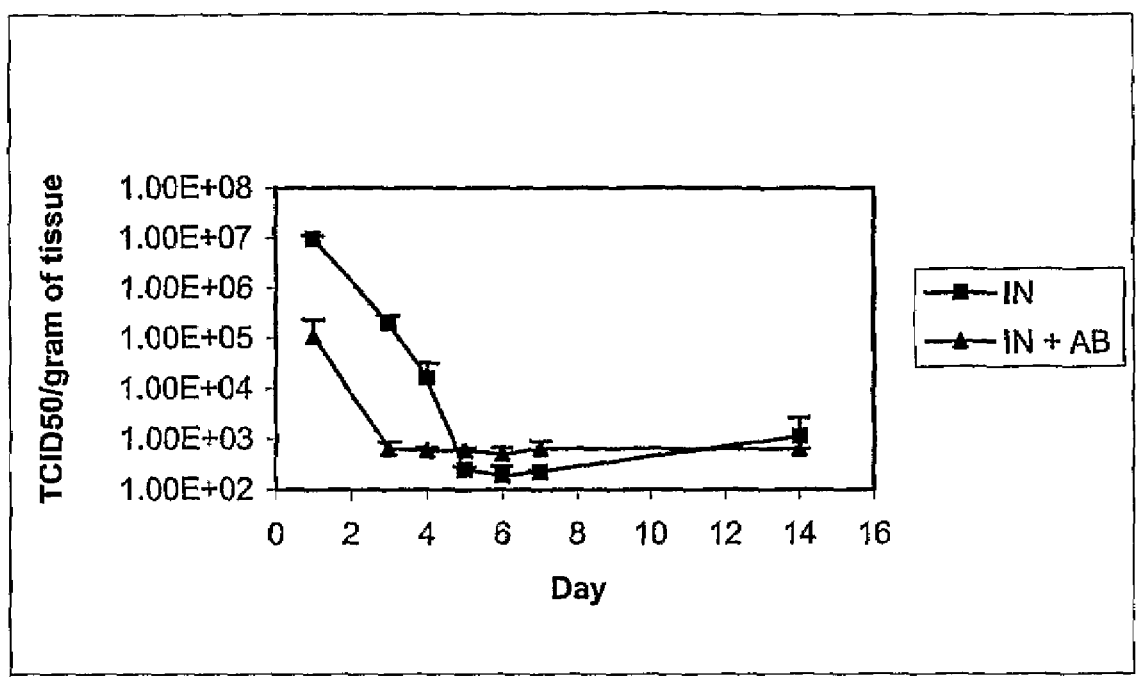

FIG. 13. Titres for lung samples collected from SARS CoV infected mice (IN and IN+AB groups) at various time points p.i., determined by TCID50. Values are expressed in TCID50/gram of tissue.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Definitions

As used herein, "neutralizing antibody" refers to an antibody, for example, a monoclonal antibody, capable of disrupting a formed viral particle or inhibiting formation of a viral particle or prevention of binding to or infection of mammalian cells with a viral particle.

As used herein, "diagnostic antibody" or "detection antibody" or "detecting antibody" refers to an antibody, for example, a monoclonal antibody, capable of detecting the presence of an antigenic target within a sample. As will be appreciated by one of skill in the art, such diagnostic antibodies preferably have high specificity for their antigenic target.

As used herein, "humanized antibodies" refer to antibodies with reduced immunogenicity in humans.

As used herein, "chimeric antibodies" refer to antibodies with reduced immunogenicity in humans built by genetically linking a non-human Variable region to human constant domains.

Described herein is the isolation, identification and characterization of a plurality of anti-SARS monoclonal antibodies.

As discussed herein, some of the monoclonal antibodies have been shown to have SARS neutralizing activity, meaning that said monoclonal antibodies, humanized or chimeric versions thereof or immunoreactive fragments thereof could be used as therapeutics for treating, preventing or ameliorating symptoms associated with SARS infection in patients in need of such treatment. The patients may be for example human.

Also described herein are methods of producing anti-SARS mAbs, for example, humanized or chimeric anti-SARS mAbs. It is of note that these mAbs may be produced in a variety of systems; for example, germline cells or transgenic plants. In these embodiments, an expression vector comprising a nucleic acid encoding an anti-SARS mAb or a humanized or chimeric version thereof or an immunoreactive fragment thereof is transformed into a suitable host and the host is grown under conditions promoting expression of the mAb which is then recovered. The mAbs may then be purified using means known in the art and used to develop pharmaceuticals, as discussed below.

As described herein, some of the monoclonal antibodies are useful for detection of SARS virus within biological samples for example, but by no means limited to, infected cells, directly on viral particle in infected cell lysates, in purified virus fractions, serum, whole blood, naso-pharengeal swabs, stool, or bronchio-alveolar lavage. As will be appreciated by one of skill in the art, individual detection monoclonal antibodies or combinations thereof may be packaged in a kit along with instructions for use, as described below.

The SARS detection monoclonal antibodies may be selected from the group consisting of: F26G1, F26G2, F26G4, F26G5, F26G6, F26G8, F26G12, F26G13, F26G14, F26G16, F26G17, F26G3, F26G7, F26G9, F26G10, G26G18 and F26G19.

The SARS neutralizing monoclonal antibodies may be selected from the group consisting of F26G3, F26G7, F26G9, F26G10, F26G18 and F26G19.

DNA and amino acid sequences for the above-referenced monoclonal antibodies may be found in FIGS. 7-10 and also in the attached sequence listing, wherein amino acid sequences of: F26G3-VH is SEQ ID No. 1; F26G7-VH is SEQ ID No. 2; F26G9-VH is SEQ ID No. 3; F26G10-VH is SEQ ID No. 4; F26G18-VH is SEQ ID No. 5; F26G19-VH is SEQ ID No. 6; F26G1-VH is SEQ ID No. 7; F26G6-VH is SEQ ID No. 8; F26G8-VH is SEQ ID No. 9; F26G3-VL is SEQ ID No. 10; F26G7-VL is SEQ ID No. 11; F26G9-VL is SEQ ID No. 12; F26G10-VL is SEQ ID No. 13; F26G18-VL is SEQ ID No. 14; F26G19-VL is SEQ ID No. 15; F26G1-VL is SEQ ID No. 16; F26G6-VL is SEQ ID No. 17; and F26G8-VL is SEQ ID No. 18; and wherein DNA sequences of: F26G3-VH is SEQ ID No. 19; F26G7-VH is SEQ ID No. 20; F26G9-VH is SEQ ID No. 21; F26G10-VH is SEQ ID No. 22; F26G18-VH is SEQ ID No. 23; F26G19-VH is SEQ ID No. 24; F26G1-VH is SEQ ID No. 25; F26G6-VH is SEQ ID No. 26; F26G8-VH is SEQ ID No. 27; F26G3-VL is SEQ ID No. 28; F26G7-VL is SEQ ID No. 29; F26G9-VL is SEQ ID No. 30; F26G10-VL is SEQ ID No. 31; F26G18-VL is SEQ ID No. 32; F26G19-VL is SEQ ID No. 33; F26G1-VL is SEQ ID No. 34; F26G6-VL is SEQ ID No. 35; and F26G8-VL is SEQ ID No. 36.

As will be appreciated by one of skill in the art, the monoclonal antibodies may be used individually or in any combination thereof.

As will be appreciated by one of skill in the art, detection antibodies must show high specificity and avidity for their antigenic target. As such, showing that a monoclonal antibody reacts with the antigenic target derived from a highly purified or in vitro prepared sample does not guarantee that the antibody has sufficient specificity for use with biological sample. That is, the monoclonal antibody must have sufficient specificity that it will not produce false positives or react with antigens from related, non-SARS coronaviridae.

Examples of suitable tests for determining utility as a diagnostic or as a neutralizing mAb include but are by no means limited to negative neutralization and/or negative detection of a non-SARS coronavirus, C-ELISA data showing competition of binding with the mouse mAbs that is being detected thereby showing that the mAbs can be used to show that an immune response to SARS has occurred in patient/animal sera, meaning that they were exposed/infected (abrogation of binding by human antibodies). Alternatively, biological material such as blood, mucus or stool with could be spiked or enriched with the virus and the monoclonal antibodies used to detect added virus in the sample, which would in turn determine limits of detection as well as other parameters of the monoclonal antibodies. Biological samples from experimentally infected animals could also be used to determine the utility of the mAbs at different stages of the infection cycle. Yet another method, although less desirable, would be testing of the patient material from the outbreak as this is scarce and hence valuable material.

In use, at least one of the detection antibodies is mixed with a biological sample under suitable conditions to promote binding of the at least one detection antibody with the antigenic target if the antigenic target is present in the biological sample. Binding of the detection antibody to an antigenic target within the sample is then detected using means known in the art, for example, by use of a labelled secondary antibody or other means discussed herein and/or known in the art.

As will be apparent to one of skill in the art, a combination of detection antibodies may be used. Furthermore, at least one of the detection antibodies or combinations thereof may be packaged in a kit for detecting SARS virus in biological samples. The kit may include instructions and additional reagents, for example, secondary antibodies, buffers, detection reagents and the like. Antibodies of the kit could be used for example in a capture ELISA wherein one or more mAb is coated onto a surface to catch and present SARS antigen from biological samples, then another prelabelled mAb is added to detect the presence of the antigen; as a control for indirect ELISA wherein a surface is coated with SARS antigen and the presence of antibody binding to the antigen is detected; for immunoflourescence; or for competition ELISA wherein SARS antigen is coated on a surface, and the ability of human or other infected/exposed animal serum antibody to prevent binding of one or more of the mAbs to the SARS antigen is measured.

The neutralizing antibodies were previously shown to react with a conformational epitope of the native virus which is abrogated upon denaturation of the virus. However, as will be appreciated by one of skill in the art, this does not guarantee that the neutralizing antibodies will be effective in either preventing virus formation or disrupting intact virus particles in vivo, that is, that the neutralizing antibodies will have therapeutic activity.

For example Maruyama et al demonstrated in vitro neutralization using monoclonal antibodies to Ebola virus and Parren et al confirmed this observation in guinea pigs; however in non-human primates there was no protection afforded by the monoclonal antibody. Furthermore, Jones et al. conducted extensive studies to identify which monoclonal antibodies were protective against infection with the bacteria *Burkholderia pseudomalei*. Whilst the in vitro neutralization is an excellent screening assay, the definitive test for neutralization is the in vivo protection assay. (Maruyama et al., J Virol. 1999; 73(7):6024-30; Parren et al., J Virol. 2002; 76 (12):6408-12; Jones et al., J Med Microbiol. 2002;51(12): 1055-62).

It has also been shown in HIV that in vitro neutralizing antibodies may not protect against primary isolate in vivo (Poignard et al., J Virol. 2003 Jan;77(1):353-65). In addition, mAbs that recognize the same region (epitope) but in different ways may have different neutralization properties, that is, one may neutralize while another may not, clearly indicating that neutralization is entirely empirical and needs to be tested. (Parren et al., J Virol. 1998 Dec;72(12):10270-4).

In another embodiment of the invention, a nucleic acid sequence encoding the neutralizing antibody as described above is subjected to humanization techniques or converted into a chimeric human molecule for generating a variant neutralizing antibody which has reduced immunogenicity in humans. Humanization techniques are well known in the art—see for example U.S. Pat. Nos. 6,309,636 and 6,407,213. Chimerics are also well known, see for example U.S. Pat. Nos. 6,461,824, 6,204,023, 6,020,153 and 6,120,767.

In one embodiment of the invention, chimeric antibodies are prepared by preparing an expression vector which comprises a nucleic acid encoding a constant region domain of a human light or heavy chain genetically linked to a nucleic acid encoding a light chain variable region selected from the group consisting of G1-light (SEQ ID No. 1); G3-light (SEQ ID No. 2); G6-light (SEQ ID No. 3); G7-light (SEQ ID No. 4); G8-light (SEQ ID No. 5); G10-light (SEQ ID No. 6); G15-light (SEQ ID No. 7) and G18-light(SEQ ID No. 8) or a heavy chain variable region selected from the group consisting of G1-heavy (SEQ ID No. 9); G3-heavy (SEQ ID No. 10); G6-heavy (SEQ ID No. 11); G15-heavy (SEQ ID No. 12) and G18-heavy (SEQ ID No. 13). It is of note that all of these sequences are shown in FIGS. 7-10.

In another embodiment of the invention, there are provided recombinant anti-SARS antibodies comprising at least one modified variable region, said region selected from the group consisting of G1-light (SEQ ID No. 1); G3-light (SEQ ID No. 2); G6-light (SEQ ID No. 3); G7-light (SEQ ID No. 4); G8-light (SEQ ID No. 5); G10-light (SEQ ID No. 6); G15-light (SEQ ID No. 7); G18-light(SEQ ID No. 8); G1-heavy (SEQ ID No. 9); G3-heavy (SEQ ID No. 10); G6-heavy (SEQ ID No. 11); G15-heavy (SEQ ID No. 12) and G18-heavy (SEQ ID No. 13) in which at least one but fewer than about 30 of the amino acid residues of said variable region has been changed or deleted without disrupting antigen binding. It is of note that all of these sequences are shown in FIGS. 7-10.

In yet other embodiments, immunoreactive fragments of any of the above-described monoclonal antibodies, chimeric antibodies or humanized antibodies are prepared using means known in the art, for example, by preparing nested deletions using enzymatic degradation or convenient restriction enzymes.

It is of note that in all embodiments describing preparation of humanized antibodies, chimeric antibodies or immunoreactive fragments of monoclonal antibodies, these antibodies are screened to ensure that antigen binding has not been disrupted. This may be accomplished by any of a variety of means known in the art, but one convenient method would involve use of a phage display library.

The nucleotide sequence encoding the variable regions of the light and heavy chains of antigen specific hybridomas represent the specificity of the anitbody. Specifically the most important regions are the CDRs (of the light and heavy chains): L1, L2, L3 and H1 H2 H3 respectively. It will be apparent to one of skill in the art that the most importance CDR domains are those that are most variable in nature and thus are recruited most specifically by a given antigen like SARS. These are L1 and H3. Residues in H3 and other CDR comprise the paratope which interacts with the epitope on the pathogen. Amino acid residues in H3 have been shown to directly interact/bind to residues of the epitope in crystal structure determinations. (Bossart-Whitaker et al., J Mol Biol. 1995 Nov 3;253(4):559-75; Chavali et al., Structure (Camb). 2003 Jul;11(7):875-85; Afonin et al., Protein Sci. 2001 Aug;10(8):1514-21; Karpusas et al., J Mol Biol. 2003 Apr 11;327(5):1031-41; Krykbaev et al., J Biol Chem. 2001 Mar 16;276(11):8149-58. Epub 2000 Nov 01; Beiboer et al., J Mol Biol. 2000 Feb 25;296(3):833-49; Haruyama et al., Biol Pharm Bull. 2002 Dec;25(12):1537-45).

It is of note that as discussed herein, the above-described neutralizing antibody or humanized variant thereof may be formulated into a pharmaceutical treatment for providing passive immunity for individuals suspected of or at risk of SARS infection comprising a therapeutically effective amount of said antibody. The pharmaceutical preparation may include a suitable excipient or carrier. See, for example, *Remington: The Science and Practice of Pharmacy*, 1995, Gennaro ed. As will be apparent to one knowledgeable in the art, the total dosage will vary according to the weight, health and circumstances of the individual as well as the efficacy of the antibody.

In another embodiment of the invention, a vaccine is prepared by recovering from a preparation of live, attenuated or recombinant SARS virus, antigens recognized by one or more monoclonal antibodies selected from the group consisting of F26G1, F26G2, F26G4, F26G5, F26G6, F26G8, F26G12, F26G13, F26G14, F26G16, F26G17, F26G3, F26G7, F26G9, F26G10, G26G18 and F26G19.

The invention will now be described according to examples; however, the invention is not limited to or by the examples.

Immunization and Virus Antigen Preparation:

For immunizations 5-6 week old female BALB/C mice were used (Charles River). The mice were injected subcutaneously (S.C.) with 50-ug of beta-propiolactone-inactivated SARS-coronavirus (Tor-3 strain) with an equal part of Complete Freund's Adjuvant [CFA, H37 Ra; Difco]), on day 1. The virus had been expanded after plaque purification in Vero-6 cell monolayers and partially purified through a sucrose cushion. Highly purified SARS-coronavirus (Tor-3) was prepared the same as above except that the viral particles were further purified using gradient centrifugation. (Highly purified SARS CoV was prepared as follows briefly, 500 ml of supernatant from SARS CoV infected Vero-6 cells was concentrated first on top of a cushion of iodixanol in a SW32 rotor (Beckman). Subsequently, the virus was mixed to form a suspension of 20% iodixanol and centrifuged in a NVT 90 rotor (Beckman) for 3.5 hours at 400,000 g. Fractions were collected from the bottom of the self-generated gradient, tested by Western immunoblot with convalescent patient serum, and the SARS CoV positive fractions were pooled and dialysed against PBS. The dialysed virus preparation was further concentrated by ultracentifugation for 1.5 hours at 150,000 g. On day 30 the mice received 50 μg of purified SARS virus antigen S.C. in Incomplete Freund's Adjuvant (IFA) in a total volume of 100 μl. On days 48 and 63, the mice received 5 μg of the same antigen in a total volume of 100 μl S.C. with IFA. Mice received a final booster injection with 5 μg of purified SARS urus in 200 μl PBS to the intra-peritoneal cavity 3 days prior to hybridoma fusion. Mice were euthanised by anaesthesia overdose and exsanguinated by cardiac puncture. The spleens were subsequently excised under aseptic conditions.

Preparation of Infected Cell Lysate

Infected Vero cells were scraped off of 162 $cm^2$ tissue culture flasks (Corning) and centrifuged for clarification. A borate saline mixture (0.05 M boric acid, 0.12 M, NaCl, 0.024 M NaOH) was used to wash the cell pellet twice and the pellet was resuspended in 2 ml borate saline+1% triton x-100 for each T162 flask. The pellet was kept at 4° C. using a water bath and sonicated for ten minutes at 50% power. The debris was pelleted via centrifugation at 10,000×g for ten minutes and the supernatant collected and stored at −20° C. in aliquots for later use.

Generation of mAbs:

Immunization of mice, removal of spleens, preparation of spleen and myeloma cells, and the fusion for hybridoma production were performed according to NCFAD standard operating procedures under IS017025. Ampules of the myeloma cell line P3X63Ag8.653 (ATCC) were thawed one week prior to fusion and grown in BD Cell Mab Quantum yield media in the presence of 8-Azaguanine (Sigma). Cells were in log-phase growth at the time of fusion. Hybridoma fusion was performed essentially as originally described (Kohler and Milstein, 1975, Nature 256: 495-497) with the following modifications. Briefly, spleens were harvested 3 days after a final boost and the splenocytes were prepared by splenic perfusion as follows. A 10 cc syringe with a 21 gauge sterile disposable needle was used to perforate the spleens under aseptic conditions. The spleen cells were perfused out of the spleen with injections of serum free BD cell Mab Quantum Yield medium (BD-Pharmingen). Two identically immunized mouse spleens were used to produce these hybridoma clones. The fusion was performed using the P3X63Ag8.653 myeloma line in log phase growth. The PEG1500, 1 ml, (Roche) was added drop-wise over one minute while gently tapping the tube containing the thoroughly washed myeloma-splenocyte pellet. The PEG was slowly diluted out over three minutes with serum free BD-Cell Mab Quantum Yield media (BD-Pharmingen). The cells were resuspended and mixed into 90 ml of Clonacell Medium D (HAT) media (Stemcell, Vancouver) containing 5 ml HCF, and plated out according to the manufacturers instructions. The plates were kept in a 37° C. incubator under 5% $CO_2$ overlay for about 10-18 days in humidified chambers. Visible colonies were picked from the plates after about 2 weeks growth and placed into 96 well plates containing 150-200 μl of complete hybridoma medium (BD-Quantum Yield) with 1×HT (Sigma), 4% Hybridoma cloning factor (Igen) and 10% FBS (Wisent). Supernatants were screened 4 days later via ELISA on purified virus as antigen. Isotyping was performed using a commercial dipstick test (Roche) according to the manufacturer's instructions. Hybridoma culture supernatants were concentrated 5-10 fold using stirred cell nitrogen concentrators (Amicon) with a 30 kilodalton cutoff membrane (Millipore).

Immunoassays

Enzyme Linked Immunosorbent Assay

Tissue culture supernatants were assayed for binding to purified SARS coronavirus in an ELISA assay when the cultured cells were confluent in the culture plates. The Costar 3690 96-well ½ well ELISA plates (Corning) were coated with either Bovine serum albumin or purified SARS-coronavirus (18-37 ng/well) in PBS overnight at 4° C. and then blocked with 0.4% BSA in PBS, for 2 hours at 37° C. The supernatant (30 μl/well) was incubated neat for 1 hour at 37° C. The ELISA plates were washed ten times with dH20 and patted dry on a paper towel. A pan-goat anti-mouse IgG-HRP antibody (Southern Biotechnology Associates) was diluted to 1:2000 in 0.2% BSA in PBS, applied to the ELISA plates for 45 minutes at 37° C., and then washed as described above. Positive binding was detected with commercial ABTS used according to the manufacturers instructions (Roche). The OD was read at 405 nm at 15 and 60 minute intervals after addition of the developing reagent. Mouse immune and preimmune sera was diluted to 1:2000 in 1.5 ml Eppendorf™ tubes (Falcon) in 2%-BSA PBS for use as controls.

Western Immunoblots

Whole virions or SARS-infected Vero cells at a total protein concentration of 1 μg per lane were loaded in criterion pre-cast gels (BIO-RAD) and electrophoresed at 200 V for 30 minutes. The proteins were transferred to Immobilon nylon membranes (Millipore) for 2 hours at room temperature at 100 volts, or at 27 volts overnight at 4° C. Blots were blocked in 3% BSA-TBS, rinsed three times with TBS, and reacted with monoclonal antibody overnight at 4° C. The antibody supernatants were reacted neat and concentrated supernatants were diluted 1:50 in 0.2% BSA-PBS. Blots were washed three times with TBS-tween-20 (0.05%) for five minutes before being incubated with secondary antibody (same as above) at 1:1000 in TBS, 0.2% BSA for 1 hour. The blots were washed as above and developed using DAB (Pierce) insoluble substrate.

Immunofluorescence Staining of Vero Cells Infected with SARS-Coronavirus

Monolayers of SARS-infected Vero cells were stained as follows. Glass slides were coated with infected Vero cell monolayers and fixed with acetone. The slides were irradiated with 20 kilogreys from a cobalt gamma irradiator, removed from biocontainment, and then stored at −80° C. Dilutions of antibodies and test sera were made initially in 96 well plates (Falcon). Samples were allowed to incubate for 45 minutes in a 37° C. incubator, and were washed with distilled water. Fluorescein labelled secondary antibodies (Sigma) diluted in PBS were added to the slides and incubated for 45 minutes at 37° C., washed as above, and air dried. Slides were coated with mounting medium and stored at 40° C. until examined.

Virus Neutralization

Plaque Reduction Virus Neutralization Assay (NML)

A standard plaque reduction neutralization test was performed as previously described (Godet et al., 1994, J. Virol. 68: 8008-8016). Briefly, mixtures of pre-titred (100 PFUs) SARS coronavirus and serial 2-fold dilutions of hybridoma supernatant were incubated at 37° C. for 1 hr and added to six well plates containing Vero cell monolayers. After a 37° C. incubation for 1 hr, a nutrient-agar overlay was added and the plates placed in a $CO_2$ incubator for approximately 3 days. A second overlay was then added which contained neutral red as a vital stain. Plates were then checked periodically over the next few days for plaque formation. The highest dilution tested that produced a plaque reduction of at least 90% was defined as the titration end point.

Cytopathic Effect (CPE) Reduction Virus Neutralization Assay (NCFAD)

The ELISA positive monoclonal antibodies were screened for cross-neutralization with other coronaviruses using microtiter format CPE reduction assay: concentrated monoclonal antibodies (hybridoma supernatants) were diluted 1:20 in cell culture medium and incubated with 100 TCID50 of either SARS HCoV (Tor-3), or transmissible gastroenteritis virus (TGEV, Diamond strain; kindly provided by Dr. Susy Carman, LSD, University of Guelph) for 1 hr at 37° C. The virus-antibody mix was then transferred onto cell monolayers in 96-well plates (Costar, Corning, N.Y.). Vero V-76 cells were used for the SARS WCoV, ST cells for the TGEV. The plates were incubated until CPE developed in virus back titration controls.

Development of mAbs to the SARS-Virus

We developed a panel of mAbs to the SARS HCoV. ELISA screening on purified SARS coronavirus identified a panel of 17 IgG/K type mAbs (FIG. 1a, table 1). The general binding reactivity of these mAbs is decreased on heat denatured purified virus preparations indicating destruction of epitopes. There is a similar decrease in binding by many of these mAbs when tested on SARS-HCoV infected vero cell lysates as antigen. Heat denaturation had little effect on the binding of mAb F26G16 which also maintains a high OD on infected lysates. This mAb does however show higher background of the irrelavant antigen bovine serum albumin (BSA) (FIG. 1a) and has inconsistent reactivity in immunoblots with heat denatured viral lysate (table 1). Immunoblot methods are less sensitive than ELISA especially when using the lower quality infected cell lysate as antigen. Unfortunately preparation of highly purified viral antigen requires enormous efforts under containment which emphasizes the need for a quality recombinant antigen assay.

Western immunoblot analysis identified mAbs to the SARS spike protein. A total of five mAbs react with the SARS-spike protein in Western immunoblots, using the whole purified virus or virus infected cell lysate (FIG. 1b). The antigen identity of the remaining 11 Western immunoblot negative mAbs could not be determined which suggests that these mAbs target conformational epitopes that are destroyed in the Western blot sample preparation and membrane transfer process. These data led us to test for biological activity in virus neutralization assays.

Immunochemical and Biological Characterization of Binding

Neutralizing antibodies to the SARS virus recognize epitopes via interaction with both conformational and linear epitopes. We identified mAbs that neutralize in vitro cell culture infectivity of the SARS-virus. Concentrated culture supernatants from four of the eleven Western immunoblot negative (conformational) mAbs were significantly neutralizing compared to irrelevant isotype-matched concentrated mAbs to other antigens (Table 1). SARS virus infectivity was neutralized with mAbs F26G3, G7, G9, G10, G18 and G19. No cross-neutralization was observed for the animal coronavirus TGEV. The remaining mAbs in our panel showed no decrease in virus growth. This result reveals that we have developed mAbs specific for epitopes on the SARS coronavirus.

Immunoblot analysis reveals a spectrum of conformational requirements for binding. We examined the effects of different denaturing treatments on binding activity of a subset of neutralizing and some non-neutralizing mAbs using immunodot blot assays on infected lysates compared to uninfected lysates. A series of conditions were tested including exposure to heat, detergent, a reducing agent, and combinations thereof. The Immunodotblot reactivities of this panel of mAbs reveals important immunochemical requirements for their respective epitopes, and are summarized in table 1. In general the conformational requirements of the neutralizing antibodies are higher than the non-neutralizing and they are less tolerant of denaturation of the epitopes. None of the mAbs react with mock-infected lysates as assayed in Immunodotblots. This suggests that the majority of the neutralizing mAbs likely target surface exposed protein epitopes on the native viral particle, which has been identified as spike protein via Western analysis for mAbs F26G18 and F26G19. This is consistent with binding data observed in ELISA on heat denatured virus infected lysate compared to native infected lysate. In this case, regardless of Western reactivity, the non-neutralizing clones retain more ability to bind to heat denatured antigens compared to neutralizing mAbs (lower mean percent reduction in OD per group p<0.001, students T test). There are exceptions, however, in that it is difficult to use traditional classifications to describe the binding properties of these mAbs as being conformational or linear according to biological activity. Interestingly, clone F26G18 binds to spike protein in Western blot and neutralizes the SARS virus and thus the binding of F26G6 cannot be termed strictly conformational in nature. This is in contrast to neutralizing mAbs produced against other enveloped viruses (Zwick et al., 2001, J. Virol. 75: 6692-6699; Wilson et al., 2000, Science 287: 1664-1666) that require the antigen to have native conformation for binding. It will be important to verify, under optimized conditions (Opstelten et al., 1995, J. Cell Biol. 131: 339-349) the use of viral lysates designed for maximal recovery of coronavirus proteins and to this end the production of high quality recombinant protein antigens will provide useful insights.

SARS-virus reactivity was confirmed for the four Western immunoblot negative, virus neutralizing mAbs (F26G3, G7, G9, G10) using an immunofluorescence assay. In order to independently confirm recognition of native SARS antigens we tested these mAbs via immunofluorescence relative to a non- neutralizing mAb F26G6, which we know recognizes Spike protein in immunohistochemical staining of infected Vero cells. The neutralizing mAbs F26G3, G7, G9, and G10 specifically recognize SARS-HCoV infected but not uninfected Vero cells in immunofluorescence (FIG. 2). Irrelevant, isotype matched mAbs, produced in an identical fashion, do not react with SARS-virus infected Vero cells. These data are consistent with the appearance of coronavirus antigens on the surface of the infected cell during replication (Talbot et al., 1984, Virology 132: 250-260) although the fixation process may allow for reactivity of these mAbs with internal antigens as well. Collectively, these data demonstrate that these mAbs will be useful for developing antigen detection systems for diagnostics.

Conclusions

Linear epitopes on the spike protein and conformational epitopes on as of yet unknown antigen(s) provide neutralizing targets on the SARS virus. These data clearly show that the spike protein is a putative protective antigen, as it is the target of neutralizing mAbs F26G18 and G19. Moreover, these mAbs could be used to identify protective epitopes for vaccine formulations (Enjuanes et al., 1995, Dev. Biol. Stand. 84: 145-152). Studies are underway to determine the identity of the additional unknown antigen(s) recognized by the other neutralizing mAbs with more conformational epitopes. Molecular studies have revealed that the RT PCR amplified V-genes of the hybridoma clones that express these neutralizing mAbs contain distinct sequences. Therefore, the hybridomas expressing the neutralizing mAbs were derived from independently rearranged and clonally selected B cells in vivo, and are not derived from the same clone. This is the first description of SARS-HCoV specific and neutralizing mAbs and these antibodies should prove useful for the development of new diagnostic tests, studies on antigenic variation, and vaccine development in the global fight against SARS, as discussed above.

Virus, Cells and Monoclonal Antibodies

Vero E6 (African Green Monkey kidney) cells were cultured in Dulbecco's modified Eagle's medium (DMEM, Sigma) with 10% heat inactivated fetal bovine serum (FBS, Gibco BRL), 1% penicillin/streptomycin and 1% L-glutamine. Cells were incubated in the presence of 5% $CO_2$ at 37° C.

The Tor3 strain of SARS CoV was isolated at the National Microbiology Laboratory from a patient infected during the initial SARS outbreak in Toronto 2003 (Weingartl et al., 2004, Emerg Infect Dis 10: 179-184). The virus stock had been expanded after plaque purification in Vero E6 cell monolayers and partially purified through a sucrose cushion ($5 \times 10^6$ pfu/ml). Preparation of the infectious SARS CoV was performed under BSL-3 containment conditions. All animal experiments and processing of infected tissues were conducted under BSL4 containment conditions. Monoclonal antibodies were generated from mice immunized with inactivated SARS CoV Tor3 strain.

Animal Studies

Female BALB/c mice 6 to 8 weeks old were obtained from Charles River (Quebec, Canada). In the first mouse study, BALB/c mice were infected with the Tor3 strain of SARS CoV by one of three routes: intraperitoneal (IP), intranasal instillation (IN) or oral gavage (OR).

IN, IP and OR groups received 20 µl, 200 µl and 100 µl of diluted virus (containing $5 \times 10^4$ plaque forming units (PFU)) respectively, all animals received the same number of PFUs. At one hour and 1, 3, 5, 7 and 9 days post infection (p.i.), mice were anaesthetized with halothane and sacrificed by cardiac puncture. Blood, spleen, liver, kidney and lungs were harvested. Organs were immediately homogenized in DMEM immediately and an aliquot was removed for RNA extraction. Remaining homogenates were stored at −80° C. for virus isolation.

In a follow-up study, two groups of female BALB/c mice (6 to 8 weeks old, approximately 20 g in weight) were injected IP, a single time, with a cocktail of 4 neutralizing antibodies (Berry et al., 2004, J Virol Methods 120: 87-96). We administered 10 µg of each antibody to the mice; the final dose of antibody was therefore 40 µg/mouse. Two hours following antibody treatment, animals were anaesthetized with halothane and were inoculated IN with $5 \times 10^5$ PFU of the Tor3 strain in 100 µl. At 1, 2, 3, 4, 5, 6, 7 and 14 days following infection, mice from the antibody treated group (IN+AB) and untreated group (IN) were weighed then anaesthetized with halothane and sacrificed by cardiac puncture. Blood, spleen, liver, kidney, lung and brain were harvested. Organs were weighed then homogenized in 1.0 ml of DMEM, aliquots were transferred to AVL RNA extraction buffer (Qiagen) and stored at −20° C. The remainder of each homogenate was stored at −80° C. for virus isolation. All animal experiments were performed under an approved animal use document and according to the guidelines of the Canadian Council on Animal Care.

RNA Extraction

RNA from the first animal experiment was extracted using the Trizol LS protocol (Invitrogen). RNA from the second animal study was extracted from tissue homogenates using Qiagen viral RNA Minikit (Qiagen). Homogenate was transferred to AVL extraction buffer and RNA was extracted following the Qiagen protocol.

Nested RT-PCR and Real-time RT-PCR

For the first mouse study, nested RT-PCR was performed using a primer set targeting the polymerase gene (L). RT-PCR was performed using a one-step RT-PCR kit (Qiagen) and primers CorV Forward1 and CorV 389 Reverse1 (Table 3) in a Biometra thermocycler. Nested PCR was done in a Biometra thermocycler using Taq DNA polymerase (Invitrogen) and primers CorV 154 Forward2 and CorV 310 Reverse2 (Table 3) with 4% of the amplicons obtained from the first round reaction. All amplicons from first and second round amplifications were verified for size. All positive amplicons from the nested round were sequenced using an ABI 3100 Genetic Analyzer.

For the second mouse study, it was necessary to use real-time RT-PCR due to the large number of samples collected. RT-PCR master mixes were made using the Taqman one-step RT-PCR mastermix (Applied Biosystems) and primers targeting the nucleoprotein gene (Table 3) in an applied biosystems 7700 thermocycler.

Virus Isolation

Virus isolation was performed on selected tissue homogenates based on PCR data. Frozen homogenates were thawed from −80° C. and centrifuged at 10,000×g for 5 minutes. Following centrifugation, supernatant was collected and mixed with 500 µl of DMEM (no supplements), and filtered using 0.22 µM filter (Millipore). Each supernatant was used to infect one 25 cm² flask of Vero E6 cells by incubation at 37° C. for 1 hour with intermittent rocking. Five ml of DMEM containing 2% FBS, 1% penicillin/streptomycin and 1% L-glutamine was added to each flask. Cells were incubated at 37° C. with 5% $CO_2$ and cytopathic effect (CPE) was monitored up to day 10 p.i. If CPE was present, supernatant was removed for testing in nested RT-PCR, followed by sequencing of amplicons.

Determination of viral load in the lung by TCID50

Tissue samples that demonstrated CPE upon first passage were chosen for TCID50 determination. Homogenized tissues in DMEM were filter sterilized using a 0.22 µM filter (Millipore) and diluted 1:100 in DMEM. Ten-fold serial dilutions from 10-2 to 10-8 were prepared in DMEM and used to infect Vero E6 cells at 80-90% confluency in 24-well plates. Media was removed from the cells and 250 µl of each dilution of virus was added to each of four wells. Virus was adsorbed to cells for 1 hour at 37° C., then 1 ml of DMEM with 2% FBS, 1% penicillin/streptomycin and L-glutamine was added per well. Infected cells were incubated at 37° C. with 5% $CO_2$ and were monitored for CPE up to day 10 p.i. The dilution of virus that caused cytopathic effect (CPE) in 50% of the well was calculated by Spearman Karber method (Spearman, 1908, Brit J Psychol 2: 227). Virus titres are expressed as the 50% tissue culture infectious dose (TCID50) per gram of tissue.

Results

SARS CoV replication in mice infected by different routes

In order to establish a small animal model for efficacy testing of antivirals, vaccines and therapeutic antibodies, BALB/c mice were infected with the Tor3 strain of SARS CoV, 5×10⁴ PFU, by one of three routes: intraperitoneal (IP), intranasal (IN) or oral (OR). Animals Were observed closely for clinical signs or symptoms over a period of nine days (1st study) and 14 days (2nd study) post virus challenge. Mice were serially sacrificed at different times p.i. and blood and organs were harvested for the detection of viral genomic RNA by RT-PCR and the presence of infectious virus by TCID50. In general, mice did not show any signs of disease, particularly not of respiratory illness. Intranasally infected animals demonstrated aggressive behaviour on days 3 and 4 p.i., however, no change in weight and grooming behaviour.

Independent of the route of infection, none of the animals were viremic at any time p.i. but virus spread systemically as indicated by replication in several organs, particularly spleen, liver and lungs (FIG. 11). Of the three infection routes, the IP route was most efficient in initiating systemic infection more rapidly. Since the IP route does not mimic human SARS CoV transmission, of the routes that are biologically relevant for human transmission (IN and OR), IN infection was most successful with highest titres in spleen and lung. Despite the fact that OR infection did result in systemic infection, virus replication was only short lived compared to the IP and IN route. Viral RNA was not detected in any of the groups or tissues at day 9 p.i. indicating that the animals had cleared SARS CoV by that time. All RT-PCR positive amplicons were sequenced and confirmed to be SARS CoV.

Spleen and lung tissue samples from the biologically relevant routes (IN and oral) were selected for virus isolation to confirm the presence of viable virus in these tissues. Following infection of Vero E6 cells with tissue homogenates, CPE was observed on day 4. PCR amplification from RNA extracted from tissue culture supernatants followed by sequence determination confirmed the isolation of SARS CoV. Thus, we confirmed establishing a systemic infection with SARS CoV in mice by three different routes of inoculation. Infection by oral gavage is interesting since earlier reports suggest the possibility that SARS CoV can infect humans via the fecal/oral route (Tang et al., 2004, CMAJ 170: 47-54; Chan et al., Emerg Infect Dis 10: 825-831).

Neutralizing antibodies reduce virus titre

Having established a proper animal model with a relevant challenge route, we next tested the neutralizing activity of several monoclonal antibodies raised against SARS CoV (Berry et al., 2004). We chose to use a 10-fold higher virus dose in a larger volume to infect the animals IN to assure a more reliable lower respiratory tract infection. Prior to IN infection of mice with SARS CoV (dose 5×10⁵ PFU), a cocktail of 4 neutralizing monoclonal antibodies (single dose) were administered IP. Animals were followed up by clinical observation and were sacrificed at different times post challenge. Tissue samples, collected post mortem were tested for the presence of viral nucleic acid by real-time RT-PCR and infectious virus by TCID50.

In accordance with the previous experiment, none of the infected animals demonstrated typical SARS illness. As demonstrated before, there was no detectable viremia, however there was systemic spread of infection, particularly to the spleen (day 2-6) and the lungs (day 1-14) in the untreated control group (FIG. 12A). In comparison, the antibody treated group showed a dramatic decrease in viral replication in the spleen and lungs from day 3 on (FIG. 12B). Viral replication was also observed in the brain on days 1 and 2 in the untreated group and only on day 1 in the antibody treated group.

To better define the neutralizing efficacy reduction in titre between the antibody treated (IN+Ab) and untreated groups (IN), titres were determined by TCID50 on lung homogenates. Mice that received the cocktail of neutralizing antibodies showed a two-log reduction in virus titre on day 1 and 3 p.i. (FIG. 13). By day 4, the IN+AB group showed a reduction in titre by one-log in comparison to the IN-group. Furthermore, the viral load data was in concordance with the viral titre data and showed between one and three logs of decrease of viral RNA in the same samples.

Discussion

This study has demonstrated that SARS CoV established a systemic infection in mice following three different routes of virus infection without detectable levels of viremia. This is in contrast to the results of Subbaro et al., who recovered virus only from the upper and lower respiratory tract following intranasal infection but not from the internal organs (Subbarai et al., 2004, J Virol 78: 3572-3577). In our study, the main target organs for viral replication were determined to be spleen and lung and, thus, are similar to those in humans (To and Lo, 2004, J Pathol 203: 740-743; Wentworth et al., 2004, Emerg Infect Dis 10: 1293-1296). The virus replicated in the respiratory tract and spread systemically infected mice continued. to gain weight and showed no signs of disease other than a marked increase is aggressive behaviour in IN infected mice on days 3 and 4 post infection viral RNA was detected in the brains of infected mice on days 1 and 2 post infection perhaps indicating limited infection via the olfactory bulb followed by inflammation on days 3 and 4 resulting in the observed aggression. We are confident that the mouse is a viable model for testing of antiviral, vaccines and immunotherapeutics as we are able to reliably induce systemic infection. However, as found by others groups protection can only be assessed by measuring reduction in virus replication (Subbarao et al., 2004), as mice are not a model for severe disease as none of the infected animals displayed typical SARS illness.

We attempted to determine if the SARS CoV could establish an infection in mice following oral inoculation. This was done in response to published data and our own observations indicating that viral RNA could be detected in human stool samples for up to 35 days, far longer than in the nasal swabs (Chan et al., 2004). In addition, the outbreak in Amoy Gardens, Hong Kong, appeared to be associated with fecal transmission raising the possibility of a fecal/oral transmission route for human SARS CoV infection (Ng, 2003, Lancet 362: 570-572; Department of Health, Hong Kong government. Outbreak of SARS at Amoy Gardens, available at http://www.info.gov.hk/info/ap/pdf/amoy_e.pdf). In our hands, the virus was clearly capable of initiating a systemic infection following oral infection with virus spread to the lungs, liver and spleen of the orally infected mice. We determined that infection via the intranasal (IN) route resulted in a more sustained and widespread respiratory and systemic infection than was observed following, either IP or oral infection and therefore, we chose to use this route for our subsequent work.

The current study demonstrated that IP administration of a single dose of a cocktail of neutralizing monoclonal antibodies prior to mucosal challenge reduced virus replication by two-logs in the first critical days p.i.. The antibody treated group showed a complete abolishment of viral RNA in all three tissues (spleen, liver, lung) 5 days after challenge while viral RNA was detected in the untreated group for up to 14 days in the lung. The ability of a single dose of neutralizing antibodies to inhibit virus replication in the lungs is promising since this is the primary site of SARS replication and disease manifestation in humans. It is likely that consecutive treatments would enhance the efficacy particularly in humans at present his would be difficult to test experimentally as both NHP and mice are capable of clearing infection with the SARS-CoV independently of treatment and so we are limited to measuring viral loads early in the infection as an indicator of efficacy.

Previous studies have shown that infection as well as transfer of hyperimmune serum protects mice from IN challenge with SARS CoV (Subbarao et al., 2004). Although hyperimmune sera may work experimentally in mice, there are several problems associated with the use of polyclonal human sera in human patients such as difficulty in finding immune donors and risks related to the use of human blood products (Traggiai et al., 2004, Nat Med 10: 871-875). Recently, Traggiai and colleagues (Traggiai et al., 2004) demonstrated that human monoclonal antibodies offer an alternative. Mice were given between 50 and 800 µg of human monoclonal antibodies IP and then challenged IN 2 days later with SARS CoV (104 TCID50). Animals that received 200 µg of the human monoclonal antibodies were protected from viral replication in the lower respiratory tract, determined by TCID50 (Traggiai et al., 2004). However, RT-PCR detection was not employed to determine the levels of viral genome present in the tissues, typically a much more sensitive approach. Furthermore, only one time point was examined (2-days p.i.) and in our experience, even when using group sizes of 5 mice, it is possible that virus detection in the lung by RT-PCR or virus titration is negative at one time but positive later. We have shown that when administering the antibody cocktail containing a total of 40 µg only 2 hours prior to challenge we can achieve a 2-log decrease in virus titre in the lung following infection with a 50× higher dose of SARS CoV ($5 \times 10^5$ PFU). It is likely that possible the dose of antibodies, pre-treating earlier and/or multiple treatments to increase the tissue levels at the time of challenge will substantially improve the performance of the therapy. Furthermore, while a synergistic effect of these SARS-neutralizing monoclonal antibodies has not yet been demonstrated, the use of a cocktail of monoclonal antibodies should limit the potential deleterious effects of antigenic variation and escape from neutralization. Examples of synergistic effects of monoclonal antibodies have been observed in the neutralization of HIV-1 in vitro (Zwick et al., 2001, J Virol 75: 12198-12208). Human monoclonal antibody therapy has also been studied in ferrets resulting in protection from SARS CoV challenge. However, at this time there appears to be little advantage in testing antibodies in this animal model (ter Meulen et al., 2004, Lancet 363: 2102-2103).

In conclusion, we have demonstrated for the first time that SARS CoV can cause systemic infection in mice when delivered by the IP, OR and IN routes. Despite the absence of any detectable viremia, viral RNA and infectious virus was primarily detected in lung and spleen. Furthermore, we have shown that administration of mouse monoclonal antibodies significantly reduces the viral load in primary target organs and protects animals from IN challenge. Thus, therapeutic antibodies have to be considered as a potential treatment option for SARS CoV infections in humans.

While the preferred embodiments of the invention have been described above, it will be recognized and understood that various modifications may be made therein, and the appended claims are intended to cover all such modifications which may fall within the spirit and scope of the invention.

TABLE 1 mAbs to the SARS HCoV Coronavirus

| Clones | Class[1] | Neutralizing Titre[2] | | Protein Target[4] | Conformational Requirement of Epitope in Immuno-dot blot[5] | | | | | | | IFA[6] | Epitope[7] |
|---|---|---|---|---|---|---|---|---|---|---|---|---|---|
| | | NML | NCFAD[3] | | N | H | D | HD | R | HR | A | | |
| F26G1 | G2a/k | 0 | 0 | Spike | + | +/− | + | − | + | +/− | − | + | L, E |
| F26G2 | G2a/k | 0 | 0 | U | nd | nd | nd | nd | nd | nd | nd | − | C |
| F26G4 | G2a/k | 0 | 0 | U | nd | nd | nd | nd | nd | nd | nd | − | C |
| F26G5 | G2a/k | 0 | 0 | Spike | + | + | +/− | +/− | + | + | +/− | +/− | L, E |
| F26G6 | G2b/k | 0 | 0 | Spike | + | + | + | +/− | + | + | + | ++ | L, E |
| F26G8 | G2a/k | 0 | 0 | Spike | + | + | + | +/− | + | + | +/− | −+ | L, E |
| F26G12 | G2a/k | 0 | 0 | U | nd | nd | nd | nd | nd | nd | nd | − | C |
| F26G13 | G2b/k | 0 | 0 | U | nd | nd | nd | nd | nd | nd | nd | +/− | C, E |

TABLE 1-continued mAbs to the SARS HCoV Coronavirus

| Clones | Class[1] | Neutralizing Titre[2] | | Protein Target[4] | Conformational Requirement of Epitope in Immuno-dot blot[5] | | | | | | | IFA[6] | Epitope[7] |
| | | NML | NCFAD[3] | | N | H | D | HD | R | HR | A | | |
|---|---|---|---|---|---|---|---|---|---|---|---|---|---|
| F26G14 | G2b/k | 0 | 0 | U | nd | nd | nd | nd | nd | nd | nd | + | C, E |
| F26G16 | G1/k | 0 | 0 | U | + | – | + | – | – | – | – | – | C |
| F26G17 | G2b/k | nd | 0 | U | nd | nd | nd | nd | nd | nd | nd | nd | C |
| F26G3 | G2a/k | >1/40 | >1/20 | U | + | – | + | – | – | – | – | + | C, E, P |
| F26G7 | G2b/k | >1/80 | >1/20 | U | + | – | + | – | +/– | – | – | + | C, E, P |
| F26G9 | G2a/k | >1/80 | >1/20 | U | + | – | +/– | – | – | – | – | + | C, E, P |
| F26G10 | G2a/k | >1/80 | >1/20 | U | + | – | +/– | – | – | – | – | ++ | C, E, P |
| F26G18 | G2b/k | nd | >1/20 | Spike | + | +/– | + | – | + | + | – | nd | L, P |
| F26G19 | G2a/k | nd | >1/20 | Spike | + | – | + | – | +/– | – | – | nd | L, P |

[1]Only IgG class antibodies were used for this study.
[2]Virus neutralization tests were performed in independent containment laboratories (NML, National Microbiology Laboratory; NCFAD, National Centre for Foreign Animal Disease) laboratories independently.
[3]Only a single dilution of 1/20 was tested in microwell format.
[4]Protein specificity tests, shown here were determined by Western immunoblot with purified virus and infected cell lysate under denaturing conditions (FIG. 1).
[5]Immunodot blot was performed using whole infected cell lysate separated into 6 different aliquots and then treated under various conditions described in methods. N, native; H, heat denatured, 95° C. for 5 minutes; D, SDS treated (2%); H + D, heated in the presence of SDS (2%): R, treated with reducing agent, betamercaptoethanol (5%); H + R, heated in the presence of reducing agent, betamercaptoethanol (5%); A, treated with heat, SDS (2%) and reducing agent betamercaptoethanol (5%).
[6]Immunfluoresence on whole cell slides infected with SARS coronavirus (see FIG. 2) ; ++strong positive reaction; +positive reaction; +/– weak positive reaction; –negative reaction.
[7]Epitope properties described as follows: L, linear or continuous epitope; E, surface exposed; C, conformational epitope; P, protective epitope in vitro; nd, not determined; neutralizing clones are emboldend; U, Unknown

TABLE 2

ELISA REACTIVITY

| Bio-Activity | mAb | Western Reactivity | Viral Lysate[a] | Denatured Lysate[b] | O.D. Reduction | | Mean[d] |
| | | | | | Fold[c] | Percent | |
|---|---|---|---|---|---|---|---|
| non-neutralizing | F26G2 | – | 0.743 | 0.424 | 1.7 | 43 | 51 |
| | F26G4 | – | 0.751 | 0.363 | 2.1 | 52 | |
| | F26G5 | – | 1.224 | 0.383 | 3.2 | 69 | |
| | F26G12 | – | 0.533 | 0.338 | 2.9 | 37 | |
| | F26G13 | – | 1.048 | 0.481 | 2.2 | 54 | |
| | F26G14 | – | 1.448 | 0.633 | 2.3 | 56 | |
| | F26G16 | – | 2.037 | 1.534 | 1.3 | 25 | |
| | F26G17 | – | 1.986 | 0.560 | 3.5 | 73

The invention claimed is:

1. Severe Acute Respiratory Syndrome (SARS) monoclonal antibody F26G18 having a light chain amino acid sequence as set forth in SEQ ID No 14 and a heavy chain amino acid sequence as set forth in SEQ ID No. 5.

2. A kit comprising monoclonal antibody G26G18 having a light chain amino acid sequence as set forth in SEQ ID No 14 and a heavy chain amino acid sequence as set forth in SEQ ID No. 5.

3. A pharmaceutical composition comprising a Severe Acute Respiratory Syndrome (SARS) neutralizing monoclonal antibody F26G18 having a light chain amino acid sequence as set forth in SEQ ID No 14 and a heavy chain amino acid sequence as set forth in SEQ ID No. 5 and a suitable excipient.

4. A method of preparing a chimeric antibody chain comprising:
   introducing an expression vector which comprises a nucleic acid encoding a constant region domain of a human light or heavy chain and a nucleic acid encoding a light chain variable region G18-light as set forth in SEQ ID No. 32 or a heavy chain-variable region G18-heavy as set forth in SEQ ID No. 23 into a suitable host cell;
   growing the host cell under conditions promoting expression of the chimeric antibody chain; and
   recovering the chimeric antibody chain.

5. A method of preparing a humanized antibody chain comprising:
   providing a nucleic acid comprising a light chain variable region G18-light as set forth in SEQ ID No. 32 or a heavy chain variable region G18-heavy as set forth in SEQ ID No. 23);
   modifying said nucleic acid such that at least one but fewer than about 30 of the amino acid residues of said variable region has been changed and/or deleted to reduce immunogenicity in humans without disrupting antigen binding;
   introducing said nucleic acid into a suitable host cell;
   growing the host cell under conditions promoting expression of the humanized antibody chain; and
   recovering the humanized antibody chain.

6. A pharmaceutical composition comprising a chimeric SARS antibody which comprises a chain made by the method of claim 4 and a suitable carrier.

7. A pharmaceutical composition comprising a humanized SARS antibody which comprises a chain made by the method of claim 5 and a suitable carrier.

8. A method of preparing a SARS antigen comprising: recovering from a preparation of live, attenuated or recombinant Severe Acute Respiratory Syndrome (SARS) virus, antigens bound to monoclonal antibody G26G18 having a light chain amino acid sequence as set forth in SEQ ID No 14 and a heavy chain amino acid sequence as set forth in SEQ ID No. 5.

9. A nucleic acid molecule encoding G18-light having a nucleotide sequence as set forth in SEQ ID No. 32 or G18-heavy having a nucleotide sequence as set forth in SEQ ID No. 23.

* * * * *

SEQUENCE LISTING

<160> NUMBER OF SEQ ID NOS: 43

<210> SEQ ID NO 1
<211> LENGTH: 133
<212> TYPE: PRT
<213> ORGANISM: Mus musculus

<400> SEQUENCE: 1

Glu Val Arg Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Asn Leu Glu Trp Ile
        35                  40                  45

Gly Gly Ile Asn Pro Asn Asn Gly Gly Thr Thr Tyr Asn Gln Lys Phe
    50                  55                  60

Lys Gly Lys Ala Thr Leu Thr Val Asp Lys Ser Ser Asn Thr Ala Tyr
65                  70                  75                  80

Met Glu Leu Arg Ser Leu Thr Ser Glu Asp Ser Ala Val Tyr Tyr Cys
                85                  90                  95

Ser Arg Gly Asp Tyr Gly Thr Ser Tyr Gly Tyr Phe Asp Val Trp Gly
            100                 105                 110

Ala Gly Thr Thr Val Thr Val Ser Ser Ala Lys Thr Thr Ala Pro Ser
        115                 120                 125

Val Tyr Pro Leu Ala
    130

<210> SEQ ID NO 2
<211> LENGTH: 128
<212> TYPE: PRT
<213> ORGANISM: Mus musculus

<400> SEQUENCE: 2

Val Glu Leu Leu Glu Ser Gly Thr Val Leu Ala Arg Pro Gly Ala Ser
1               5                   10                  15

Val Lys Met Ser Cys Glu Ala Ser Gly Tyr Thr Phe Thr Thr Tyr Trp
            20                  25                  30

Met His Trp Ile Lys Gln Arg Pro Gly Gln Gly Leu Glu Trp Ile Gly
        35                  40                  45

Ala Ile Tyr Pro Gly Asn Ser Asp Thr Thr Tyr Asn Gln Lys Phe Lys
    50                  55                  60

Gly Lys Ala Lys Leu Thr Ala Val Thr Ser Thr Ser Thr Ala Tyr Met
65                  70                  75                  80

Glu Leu Ser Ser Leu Thr Asn Glu Asp Ser Ala Val Tyr Tyr Cys Thr
                85                  90                  95

Arg Glu Gly Ile Pro Gln Leu Leu Arg Thr Met Asp Tyr Trp Gly Gln
            100                 105                 110

Gly Thr Ser Val Thr Val Ser Ser Ala Lys Thr Thr Pro Pro Ser Val
        115                 120                 125

<210> SEQ ID NO 3
<211> LENGTH: 127
<212> TYPE: PRT
<213> ORGANISM: Mus musculus

<400> SEQUENCE: 3

```
Val Gln Leu Leu Glu Ser Gly Thr Val Leu Ala Arg Pro Gly Ala Ser
1               5                   10                  15

Val Lys Met Ser Cys Lys Ala Ser Gly Tyr Ser Phe Thr Ser Tyr Trp
            20                  25                  30

Met His Trp Val Lys Gln Arg Pro Gly Gln Gly Leu Glu Trp Ile Gly
        35                  40                  45

Ala Ile Tyr Pro Gly Asn Ser Asp Thr Ser Tyr Asn Gln Lys Phe Lys
    50                  55                  60

Gly Lys Ala Lys Leu Thr Ala Val Thr Ser Ala Ser Thr Ala Tyr Met
65                  70                  75                  80

Glu Leu Ser Ser Leu Thr Asn Glu Asp Ser Ala Val Tyr Tyr Cys Thr
                85                  90                  95

Arg Ser Val Tyr Tyr Gly Tyr Gly Tyr Phe Asp Val Trp Gly Ala Gly
            100                 105                 110

Thr Thr Val Thr Val Ser Ser Ala Lys Thr Thr Pro Pro Ser Val
            115                 120                 125
```

<210> SEQ ID NO 4
<211> LENGTH: 226
<212> TYPE: PRT
<213> ORGANISM: Mus musculus

<400> SEQUENCE: 4

```
Glu Val Gln Leu Glu Glu Ser Gly Thr Val Leu Ala Arg Pro Gly Ala
1               5                   10                  15

Ser Val Lys Met Ser Cys Lys Ala Ser Gly Tyr Ser Phe Thr Ser Tyr
            20                  25                  30

Trp Met His Trp Val Lys Gln Arg Pro Gly Gln Gly Leu Asp Trp Ile
        35                  40                  45

Gly Ala Ile Tyr Pro Glu Asn Ser Asp Thr Ser Tyr Asn Gln Lys Phe
    50                  55                  60

Lys Gly Lys Ala Lys Leu Thr Ala Val Thr Ser Ala Ser Thr Ala Tyr
65                  70                  75                  80

Met Glu His Ser Ser Leu Thr Asn Glu Asp Ser Ala Val Tyr Tyr Cys
                85                  90                  95

Thr Arg Ser Val Tyr Tyr Gly Tyr Gly Tyr Phe Asp Val Trp Gly Ala
            100                 105                 110

Gly Thr Thr Val Thr Val Ser Ser Ala Lys Thr Thr Ala Pro Ser Val
            115                 120                 125

Tyr Pro Leu Ala Pro Val Cys Gly Asp Thr Thr Gly Ser Ser Val Thr
            130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
            195                 200                 205

Ser Ser Thr Lys Val Asp Lys Lys Ile Glu Pro Arg Val Pro Thr Ser
            210                 215                 220

Gln Asn
225
```

<210> SEQ ID NO 5

<211> LENGTH: 131
<212> TYPE: PRT
<213> ORGANISM: Mus musculus

<400> SEQUENCE: 5

```
Leu Val Gln Leu Glu Glu Ser Gly Thr Val Leu Pro Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Asn Ser Asp Thr Asn Tyr Asn Gln Lys Phe
    50                  55                  60

Lys Gly Arg Ala Thr Leu Thr Ala Val Thr Ser Thr Ser Thr Ala Ser
65                  70                  75                  80

Met Glu Leu Ser Ser Leu Thr Asn Glu Asp Ser Ala Val Tyr Tyr Cys
                85                  90                  95

Thr Arg Asp Gly Tyr Gly Ser Leu Tyr Tyr Ala Met Asp Phe Trp
            100                 105                 110

Gly Gln Gly Thr Ser Val Thr Val Ser Ser Ala Lys Thr Thr Ala Pro
            115                 120                 125

Ser Val Lys
    130
```

<210> SEQ ID NO 6
<211> LENGTH: 133
<212> TYPE: PRT
<213> ORGANISM: Mus musculus

<400> SEQUENCE: 6

```
Glu Val Gln Leu Glu Glu Ser Gly Thr Val Leu Ala Arg Pro Gly Ala
1               5                   10                  15

Ser Val Lys Met Ser Cys Lys Ala Ser Gly Tyr Thr Phe Thr Thr Tyr
            20                  25                  30

Arg Met His Trp Ile Lys Gln Arg Pro Gly Gln Gly Leu Glu Trp Ile
        35                  40                  45

Gly Ala Ile Tyr Pro Gly Asn Ser Asp Thr Thr Tyr Asn Gln Lys Phe
    50                  55                  60

Lys Asp Lys Ala Lys Leu Thr Ala Val Thr Ser Ser Ser Ala Tyr
65                  70                  75                  80

Met Glu Leu Ser Ser Leu Thr Asn Glu Asp Ser Ala Val Tyr Phe Cys
                85                  90                  95

Thr Arg Glu Gly Ile Pro Gln Leu Leu Arg Thr Leu Asp Tyr Trp Gly
            100                 105                 110

Gln Gly Thr Ser Val Thr Val Ser Ser Ala Lys Thr Thr Ala Pro Ser
            115                 120                 125

Val Tyr Pro Leu Ala
    130
```

<210> SEQ ID NO 7
<211> LENGTH: 130
<212> TYPE: PRT
<213> ORGANISM: Mus musculus

<400> SEQUENCE: 7

```
Glu Val Gln Leu Glu Glu Ser Gly Pro Gly Leu Val Ala Pro Ser Gln
1               5                   10                  15
```

```
Ser Leu Ser Ile Thr Cys Thr Val Ser Gly Phe Ser Leu Thr Asn Tyr
            20                  25                  30

Asp Ile Ser Trp Ile Arg Gln Pro Gly Lys Gly Leu Glu Trp Leu
        35                  40                  45

Gly Ile Ile Trp Thr Gly Gly Thr Ser Tyr Asn Ser Ala Phe Met
 50                  55                  60

Ser Arg Leu Ser Ile Ser Lys Asp Asn Ser Lys Ser Gln Val Phe Leu
 65                  70                  75                  80

Lys Met Asn Ser Leu Gln Thr Asp Thr Ala Ile Tyr Tyr Cys Val
                85                  90                  95

Arg Asp Arg Val Tyr Tyr Phe Pro Met Asp Tyr Trp Gly Gln Gly Thr
                100                 105                 110

Ser Val Thr Val Ser Ser Ala Lys Thr Thr Ala Pro Ser Val Tyr Pro
        115                 120                 125

Leu Ala
    130

<210> SEQ ID NO 8
<211> LENGTH: 139
<212> TYPE: PRT
<213> ORGANISM: Mus musculus

<400> SEQUENCE: 8

Met Glu Trp Ser Trp Val Phe Leu Phe Leu Val Ala Thr Ala Thr Asp
 1               5                  10                  15

Val His Ser Gln Val Gln Leu Gln Gln Pro Gly Ala Glu Leu Val Lys
                20                  25                  30

Pro Gly Ala Ser Val Lys Val Ser Cys Lys Ala Ser Gly Tyr Thr Phe
            35                  40                  45

Thr Asn Tyr Trp Ile His Trp Val Lys Gln Arg Pro Gly Gln Gly Leu
 50                  55                  60

Glu Trp Ile Gly Glu Ile Asn Pro Gly Asn Gly Arg Thr Asn Tyr Asn
 65                  70                  75                  80

Gly Asn Phe Met Asn Lys Ala Thr Leu Thr Val Asp Lys Ser Ser Asn
                85                  90                  95

Thr Ala Tyr Met Gln Leu Ser Ser Leu Thr Ser Glu Asp Ser Ala Val
                100                 105                 110

Tyr His Cys Ala Arg Leu Asp Tyr Trp Gly Gln Gly Thr Thr Leu Thr
        115                 120                 125

Val Ser Ala Lys Thr Thr Pro Pro Ser Val
    130                 135

<210> SEQ ID NO 9
<211> LENGTH: 123
<212> TYPE: PRT
<213> ORGANISM: Mus musculus

<400> SEQUENCE: 9

Val Gln Leu Leu Glu Ser Gly Ala Glu Leu Val Lys Pro Gly Ala Ser
 1               5                  10                  15

Val Lys Val Ser Cys Lys Ala Ser Gly Tyr Thr Phe Thr Ser Tyr Trp
                20                  25                  30

Ile His Trp Val Lys Gln Arg Pro Gly Gln Gly Leu Glu Trp Ile Gly
            35                  40                  45

Glu Ile Asn Pro Ser Asn Gly Arg Thr Asn Tyr Asn Gly Asn Phe Glu
 50                  55                  60
```

```
Ser Lys Ala Thr Leu Thr Val Asp Lys Ser Ser Asn Thr Ala Tyr Met
 65                  70                  75                  80

His Leu Ser Ser Leu Thr Tyr Glu Asp Ser Ala Val Tyr His Cys Thr
                 85                  90                  95

Arg Leu Asp Tyr Trp Gly Gln Gly Thr Thr Leu Thr Val Ser Ser Ala
            100                 105                 110

Lys Thr Thr Ala Pro Ser Val Tyr Pro Leu Ala
        115                 120
```

<210> SEQ ID NO 10
<211> LENGTH: 120
<212> TYPE: PRT
<213> ORGANISM: Mus musculus

<400> SEQUENCE: 10

```
Asp Ile Leu Met Thr Gln Ser Pro Thr Ser Phe Ala Val Ser Leu Gly
 1               5                  10                  15

Gln Arg Ala Thr Ile Ser Cys Arg Thr Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
 50                  55                  60

Arg Phe Ser Gly Ser Gly Ser Gly Ser Asp Phe Thr Leu Asn Ile His
 65                  70                  75                  80

Pro Val Glu Glu Gly Asp Thr Ala Thr Tyr Tyr Cys Gln His Ser Trp
                 85                  90                  95

Glu Ile Pro Cys Ala Phe Gly Gly Gly Thr Lys Leu Glu Ile Lys Arg
            100                 105                 110

Ala Asp Ala Ala Pro Thr Val Ser
        115                 120
```

<210> SEQ ID NO 11
<211> LENGTH: 116
<212> TYPE: PRT
<213> ORGANISM: Mus musculus

<400> SEQUENCE: 11

```
Glu Leu Val Met Thr Gln Ser Pro Ser Ser Leu Ser Ala Ser Leu Gly
 1               5                  10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
 50                  55                  60

Ser Arg Ser Gly Ser Asp Tyr Ser Leu Thr Ile Ser Ser Leu Glu Ser
 65                  70                  75                  80

Glu Asp Phe Ala Asp Tyr Tyr Cys Leu Gln Tyr Ile Ser Tyr Pro Trp
                 85                  90                  95

Thr Phe Gly Gly Gly Thr Lys Leu Glu Ile Lys Arg Ala Asp Ala Ala
            100                 105                 110

Pro Thr Val Ser
        115
```

<210> SEQ ID NO 12
<211> LENGTH: 116

```
<212> TYPE: PRT
<213> ORGANISM: Mus musculus

<400> SEQUENCE: 12

Asp Ile Leu Met Thr Gln Ser His Lys Cys Met Ser Thr Ser Val Gly
1               5                   10                  15

Asp Arg Val Ser Ile Thr Cys Lys Ala Ser Gln Asp Val Ser Thr Ala
            20                  25                  30

Val Val Trp Tyr Gln Gln Lys Pro Gly Gln Phe Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Thr Thr Pro Tyr
                85                  90                  95

Thr Phe Gly Gly Gly Thr Lys Leu Glu Ile Lys Arg Ala Asp Ala Ala
            100                 105                 110

Pro Thr Val Ser
        115

<210> SEQ ID NO 13
<211> LENGTH: 116
<212> TYPE: PRT
<213> ORGANISM: Mus musculus

<400> SEQUENCE: 13

Asp Ile Leu Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Tyr
                85                  90                  95

Thr Phe Gly Gly Gly Thr Lys Leu Glu Ile Lys Arg Ala Asp Ala Ala
            100                 105                 110

Pro Thr Val Ser
        115

<210> SEQ ID NO 14
<211> LENGTH: 127
<212> TYPE: PRT
<213> ORGANISM: Mus musculus

<400> SEQUENCE: 14

Glu Leu Val Met Thr Gln Ser Pro Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ala Gly Val Pro Ser Arg Phe Ser Gly
```

```
                50                  55                  60
Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Tyr Thr Leu Pro Tyr
                 85                  90                  95

Thr Phe Gly Gly Gly Thr Lys Leu Glu Ile Lys Arg Ala Asp Ala Ala
            100                 105                 110

Pro Thr Val Ser Lys Gly Glu Phe Gln His Thr Gly Gly Arg Tyr
            115                 120                 125
```

<210> SEQ ID NO 15
<211> LENGTH: 115
<212> TYPE: PRT
<213> ORGANISM: Mus musculus

<400> SEQUENCE: 15

```
Asp Ile Leu Met Thr Gln Ser Pro Ser Ser Leu Ser Ala Ser Leu Gly
  1               5                  10                  15

Glu Arg Val Ser Leu Thr Cys Arg Ala Ser Gln Glu Ile Ser Gly Tyr
                 20                  25                  30

Leu Ser Trp Leu Gln Glu Lys Pro Asp Gly Thr Ile Lys Arg Leu Ile
             35                  40                  45

Tyr Ala Ala Ser Thr Leu Asp Ser Gly Val Pro Lys Arg Phe Ser Gly
 50                  55                  60

Ser Arg Ser Gly Ser Asp Tyr Ser Leu Thr Ile Ser Ser Leu Glu Ser
 65                  70                  75                  80

Glu Asp Phe Ala Asp Tyr Tyr Cys Leu Gln Tyr Val Ser Tyr Pro Trp
                 85                  90                  95

Thr Phe Gly Gly Gly Thr Lys Leu Glu Ile Lys Arg Ala Asp Ala Ala
            100                 105                 110

Pro Thr Val
        115
```

<210> SEQ ID NO 16
<211> LENGTH: 110
<212> TYPE: PRT
<213> ORGANISM: Mus musculus

<400> SEQUENCE: 16

```
Glu Leu Val Met Thr Gln Ser Pro Val Ser Ile Thr Ala Ser Arg Gly
  1               5                  10                  15

Glu Lys Val Thr Ile Thr Cys Arg Ala Ser Ser Ser Ile Ser Ser Asn
                 20                  25                  30

Tyr Leu His Trp Tyr Gln Gln Lys Pro Gly Ser Ser Pro Lys Leu Leu
             35                  40                  45

Ile Tyr Arg Thr Ser Ile Leu Ala Ser Gly Val Leu Asp Thr Phe Ser
 50                  55                  60

Gly Ser Gly Ser Glu Ser Ser Tyr Thr Leu Thr Ile Ser Cys Met Gln
 65                  70                  75                  80

Asp Glu Val Ala Ala Thr Tyr Tyr Cys Gln Gln Gly Ser Ser Ser Pro
                 85                  90                  95

Pro His Val Arg Arg Gly Asp Gln Ala Gly Asn Lys Thr Gly
            100                 105                 110
```

<210> SEQ ID NO 17
<211> LENGTH: 116
<212> TYPE: PRT

<213> ORGANISM: Mus musculus

<400> SEQUENCE: 17

```
Glu Leu Val Met Thr Gln Ser Pro Ala Ser Leu Ser Val Ala Thr Gly
1               5                   10                  15

Lys Lys Val Thr Ile Arg Cys Ile Ser Ser Thr Asp Ile Asp Asp Asp
            20                  25                  30

Met Asn Trp Tyr Gln Gln Lys Ala Gly Lys Pro Pro Lys Leu Leu Ile
        35                  40                  45

Ser Glu Gly Asn Ile Phe Ser Pro Gly Val Pro Ser Arg Phe Ser Ser
    50                  55                  60

Ser Gly Asn Gly Thr Asp Phe Val Phe Thr Val Glu Asn Thr Leu Ser
65                  70                  75                  80

Glu Asp Val Ala Asp Asn Tyr Cys Leu Gln Ser Asp Asn Met Pro Phe
                85                  90                  95

Thr Phe Gly Ser Gly Thr Lys Leu Gly Ile Lys Arg Ala Asp Ala Ala
            100                 105                 110

Pro Thr Val Ser
        115
```

<210> SEQ ID NO 18
<211> LENGTH: 116
<212> TYPE: PRT
<213> ORGANISM: Mus musculus

<400> SEQUENCE: 18

```
Glu Leu Val Met Thr Gln Ser Pro Ala Ser Leu Ser Val Ile Thr Gly
1               5                   10                  15

Lys Lys Val Thr Ile Arg Cys Ile Ser Asn Thr Asp Ile Asp Asp Asp
            20                  25                  30

Leu Asn Trp Ser Gln Leu Lys Ala Gly Glu Pro Pro Lys Leu Leu Ile
        35                  40                  45

Ser Glu Gly Asn Ile Phe Ser Pro Gly Val Pro Ser Arg Phe Ser Ser
    50                  55                  60

Ser Gly Asn Gly Thr Asp Phe Val Phe Thr Ile Glu Asn Thr Leu Ser
65                  70                  75                  80

Glu Asp Val Ala Asn Asn Tyr Cys Phe Gln Ser Asp Asn Met Pro Phe
                85                  90                  95

Thr Phe Gly Ser Gly Thr Lys Leu Glu Ile Lys Arg Ala Asp Ala Ala
            100                 105                 110

Pro Thr Val Ser
        115
```

<210> SEQ ID NO 19
<211> LENGTH: 457
<212> TYPE: DNA
<213> ORGANISM: Mus musculus

<400> SEQUENCE: 19

```
atggaatgga gctgggtctt tctctttctc ctgtcaggaa ctgcaggtgt cctctctgag      60
gtccggctgc aacagtctgg acctgaactg gtgaagcctg ggcttcagt gaagatatcc     120 tgcaagactt ctggatacac attcactgaa tacaccatgc actgggtgaa gcagagccat     180
ggaaagaacc ttgagtggat tggaggtatt aatcctaata tggtggtac tacctacaac     240 cagaagtttta aggcaaggc cacattgact gtagacaagt cctccaacac agcctacatg     300
gagctccgca gcctgacatc tgaggattct gcagtctatt attgttcaag agggactac     360
```

```
ggtactagct acgggtactt cgatgtctgg ggcgcaggga ccacggtcac cgtctcctca    420
gccaaaacaa cagccccatc ggtctatcca ctggcca                             457

<210> SEQ ID NO 20
<211> LENGTH: 385
<212> TYPE: DNA
<213> ORGANISM: Mus musculus

<400> SEQUENCE: 20
gtggagctgc tcgagtcagg gactgtgctg gcaaggcctg ggcttcagt gaagatgtcc      60 tgcgaggctt ctggctacac ctttaccacc tactggatgc actggataaa acagaggcct   120
ggacagggtc tggaatggat tggcgctatt tatccaggaa atagtgatac tacctacaac   180
cagaagttca agggcaaggc caaactgact gcagtcacat ccaccagcac tgcctacatg   240
gagctcagca gcctgacaaa tgaggactct gcggtctatt actgtacaag agagggaatt   300
ccccaattac ttcggactat ggactactgg ggtcaaggga cctcagtcac cgtctcctca   360
gccaaaacaa caccccatc ggtca                                          385

<210> SEQ ID NO 21
<211> LENGTH: 381
<212> TYPE: DNA
<213> ORGANISM: Mus musculus

<400> SEQUENCE: 21
gtccagctgc tcgagtctgg gactgtgctg gcaaggcctg ggcttccgt gaagatgtcc      60 tgcaaggctt ctggctacag ctttaccagc tactggatgc actgggtaaa acagaggcct   120
ggacagggtc tagaatggat tggtgctatt tatcctggaa atagtgatac tagctacaac   180
cagaagttca agggcaaggc caaactgact gcagtcacat ccgccagtac tgcctacatg   240
gagctcagca gcctgacaaa tgaggactct gcggtctatt actgtacaag atccgtttac   300
tacggctacg ggtacttcga tgtctggggc cagggaccca cggtcaccgt ctcctcagcc   360
aaaacaacac ccccatcggt c                                             381

<210> SEQ ID NO 22
<211> LENGTH: 678
<212> TYPE: DNA
<213> ORGANISM: Mus musculus

<400> SEQUENCE: 22
gaggtgcagc tggaggagtc tgggactgtg ctggcaaggc ctggggcttc cgtgaagatg      60
tcctgcaagg cttctggcta cagctttacc agctactgga tgcactgggt aaaacagagg   120
cctggacagg gtctagattg gattggtgct atttatcctg aaaatagtga tactagctac   180
aaccagaagt tcaagggcaa ggccaaactg actgcagtca catccgccag cactgcctac   240
atggagcaca gcagcctgac aaatgaggac tctgcggtct attactgtac aagatccgtt   300
tactacggct acgggtactt cgatgtctgg ggcgcaggga ccacggtcac cgtctcctca   360
gccaagacaa cagccccatc ggtctatcca ctggcccctg tgtgtggaga tacaactggc   420
tcctcggtga ctctaggatg cctggtcaag ggttatttcc ctgagccagt gaccttgacc   480
tggaactctg gatccctgtc cagtggtgtg cacaccttcc cagctgtcct gcagtctgac   540
ctctacaccc tcagcagctc agtgactgta acctcgagca cctggcccag ccagtccatc   600
acctgcaatg tggcccaccc ggcaagcagc accaaggtgg acaagaaaat tgagcccaga   660
```

```
gtgcccacta gtcagaac                                                     678

<210> SEQ ID NO 23
<211> LENGTH: 398
<212> TYPE: DNA
<213> ORGANISM: Mus musculus

<400> SEQUENCE: 23
ttggtgcagc tggaggagtc tgggactgtg ttgccaaggc ctggggcttc agtgaagatg        60
tcctgcaagg cttctggcta cacctttacc agctactgga tgcactgggt aaaacagagg       120
cctggacagg tctggaatg gattggcgct atttatcctg gaaatagtga tactaactac        180
aaccagaagt tcaagggcag ggccacactg actgcagtca catccaccag cactgcctcc       240
atggagctca gcagcctgac aaatgaggac tctgcggtct attactgtac aagagacggc       300
tatggtagcc tttattacta tgctatggac ttctggggtc aaggaacctc agtcaccgtc       360
tcctcagcca aaacaacagc cccatcggtc aagggcga                              398

<210> SEQ ID NO 24
<211> LENGTH: 399
<212> TYPE: DNA
<213> ORGANISM: Mus musculus

<400> SEQUENCE: 24
gaggtgcagc tggaggagtc tgggactgtg ctggcaaggc ctggggcttc agtgaagatg        60
tcctgcaagg cttctggcta cacctttacc acctaccgga tgcactggat aaaacagagg       120
cctggacagg tctggaatg gattggcgct atttatcctg gaaatagtga tactacctac        180
aaccagaagt tcaaggacaa ggccaaactg actgcagtca catccaccag ctctgcctac       240
atggagctca gcagcctgac aaatgaggac tctgcggtct atttctgtac aagagaggga       300
attccccaat tacttcggac tttggactac tggggtcaag gaacctcagt caccgtctcc       360
tcagccaaaa caacagcccc atcggtctat ccactggcc                              399

<210> SEQ ID NO 25
<211> LENGTH: 392
<212> TYPE: DNA
<213> ORGANISM: Mus musculus

<400> SEQUENCE: 25
tgaggtgcag ctggaggagt caggacctgg cctggtggcg ccctcacaga gcctgtccat        60
tacctgcact gtctctgggt tctcattaac gaactatgat ataagctgga ttcgccagcc       120
accaggaaag ggtctggagt ggcttggaat aatatggact ggtggaggca caagttataa       180
ttcagctttc atgtccagac tgagcatcag caaggacaac tccaagagcc aagttttctt       240
aaaaatgaac agtctgcaaa ctgatgacac agccatatat tactgtgtaa gagatagggt       300
ctactacttc cctatggact actggggtca aggaacctca gtcaccgtct cctcagccaa       360
aacaacagcc ccatcggtct atccactggc ca                                    392

<210> SEQ ID NO 26
<211> LENGTH: 417
<212> TYPE: DNA
<213> ORGANISM: Mus musculus

<400> SEQUENCE: 26
atggaatgga gctgggtctt tctctttttg gtagcaacag ctacagatgt ccactcccag        60
gtccaactgc agcagcctgg ggctgaactg gtgaagcctg ggcttcagt gaaagtgtcc       120
```

```
tgcaaggctt ctggctacac cttcaccaac tactggatac actgggtgaa gcagaggcct      180
ggacagggcc ttgagtggat tggagagatt aatcctggca acggtcgtac taactataat      240
gggaacttca tgaacaaggc cacactgact gtagacaaat cctccaacac agcctacatg      300
caactcagca gcctgacatc tgaggactct gcggtctatc actgtgcaag attagactac      360
tggggccaag gcaccactct cacagtctcc tcagccaaaa caacaccccc atcggtc         417

<210> SEQ ID NO 27
<211> LENGTH: 369
<212> TYPE: DNA
<213> ORGANISM: Mus musculus

<400> SEQUENCE: 27
gtccagctgc tcgagtctgg ggctgaactg gtgaagcctg ggcttcagt gaaagtgtcc       60 tgcaaggctt ctggctacac cttcaccagc tactggatac actgggtgaa gcagaggcct     120
ggacagggcc ttgagtggat tggagagatt aatcctagca acggtcgtac taactataat     180
gggaacttcg agagcaaggc cacactgact gtagacaaat cctccaacac agcctacatg     240
cacctcagca gcctgacata tgaggactct gcggtctatc actgtacaag attagactac     300
tggggccaag gcaccactct cacagtctcc tcagccaaaa caacagcccc atcggtctat     360
ccactggcc                                                             369

<210> SEQ ID NO 28
<211> LENGTH: 380
<212> TYPE: DNA
<213> ORGANISM: Mus musculus

<400> SEQUENCE: 28
gggcccagcc ggccgagctc gacattctga tgacccagtc tcctacttcc tttgctgtat      60
ctctggggca gagggccacc atctcatgca ggaccagcca agtgtcagt acatctagct      120 atagttatat gcactggtac caacagaaac caggacagcc acccaaactc ctcatcaagt     180
atgcatccaa cctagaatct ggggtccctg ccaggttcag tggcagtggg tctgggtcag     240
acttcaccct caacatccat cctgtggagg agggggatac tgcaacatat tactgtcagc     300
acagttggga gattccgtgc gcgttcggag gggggaccaa gctggaaata aaacgggctg     360
atgctgcacc aactgtatcc                                                 380

<210> SEQ ID NO 29
<211> LENGTH: 359
<212> TYPE: DNA
<213> ORGANISM: Mus musculus

<400> SEQUENCE: 29
gtgccagatg tgagctcgtg atgacccagt ctccatcctc cttatctgcc tctctgggag      60
aaagagtcag tctcacttgt cgggcaagtc aggaaattag tggttattta agctggcttc     120
agcagaaacc agatggaact attaaacgcc tgatctacgc cgcatccact ttagattcgg     180
gtgtcccaaa aaggttcagt ggcagtaggt ctgggtcaga ttattctctc accatcagca     240
gccttgagtc tgaagatttt gcagactatt actgtctaca atatattagt tatccgtgga     300
cgttcggggg aggtaccaag ctggaaatca aacgggctga tgctgcacca actgtatcc     359

<210> SEQ ID NO 30
<211> LENGTH: 348
<212> TYPE: DNA
```

<213> ORGANISM: Mus musculus

<400> SEQUENCE: 30

```
gacattctga tgacccagtc tcacaaatgc atgtccacat cagtaggaga cagggtcagc    60
atcacctgca aggccagtca ggatgtgagt actgctgtag tctggtatca acaaaaacca   120
gggcaatttc ctaaactact gatttactgg gcatccaccc ggcacactgg agtccctgat   180
cgcttcacag gcagtggatc tgggacagat tatactctca ccatcagcag tgtgcaggct   240
gaagacctgg cactttatta ctgtcagcaa cattatacca ctccgtacac gttcggaggg   300
gggaccaagc tggaaataaa acgggctgat gctgcaccaa ctgtatcc                348
```

<210> SEQ ID NO 31
<211> LENGTH: 368
<212> TYPE: DNA
<213> ORGANISM: Mus musculus

<400> SEQUENCE: 31

```
gggcccagcc ggccgagctc gacattctga tgacccagtc tcacaaattc atgtccacat    60
cagtaggaga cagggtcagc atcacctgca aggccagtca ggatgtgagt actgctgtag   120
cctggtatca acaaaaacca gggcaatctc ctaaactact gatttactgg gcatccaccc   180
ggcacactgg agtccctgat cgcttcacag gcagtggatc tgggacagat tatactctca   240
ccatcagcag tgtgcaggct gaagacctgg cactttatta ctgtcagcaa cattatagca   300
ctccgtacac gttcggaggg gggaccaagc tggaaataaa acgggctgat gctgcaccaa   360
ctgtatcc                                                            368
```

<210> SEQ ID NO 32
<211> LENGTH: 350
<212> TYPE: DNA
<213> ORGANISM: Mus musculus

<400> SEQUENCE: 32

```
gagctcgtga tgacccagtc tccatcctcc ctgtctgcct ctctgggaga cagagtcacc    60
atcagttgca gggcaagtca ggacattagc aattatttaa actggtatca gcagaaacca   120
gatggaactg ttaaactcct gatctattac acatcaagat tacacgcagg agtcccatca   180
aggttcagtg gcagtgggtc tggaacagat tattctctca ccattagcaa cctggagcaa   240
gaagatattg ccacttactt ttgccaacag ggttatacgc ttccgtacac gttcggaggg   300
gggaccaagc tggaaataaa acgggctgat gctgcaccaa ctgtatccaa               350
```

<210> SEQ ID NO 33
<211> LENGTH: 345
<212> TYPE: DNA
<213> ORGANISM: Mus musculus

<400> SEQUENCE: 33

```
gacattctga tgacccagtc tccatcctcc ttatctgcct ctctgggaga aagagtcagt    60
ctcacttgtc gggcaagtca ggaaattagt ggttacttaa gctggcttca ggagaaacca   120
gatggaacta ttaaacgcct gatctacgcc gcttccactt agattctggt gtcccaaaa   180
aggttcagtg gcagtaggtc tgggtcagat tattctctca ccatcagcag ccttgagtct   240
gaagattttg cagactatta ctgtctacaa tatgttagtt atccgtggac gttcggtgga   300
ggcaccaagc tggaaatcaa acgggctgat gctgcaccaa ctgta                   345
```

<210> SEQ ID NO 34
<211> LENGTH: 364
<212> TYPE: DNA
<213> ORGANISM: Mus musculus

<400> SEQUENCE: 34

| | |
|---|---|
| gtgccagatg tgagctcgtg atgacccagt ctccagtatc cataactgca tctcgagggg | 60 |
| agaaggtcac catcacctgc cgtgccagct caagtataag ttccaattac ttacactggt | 120 |
| accagcagaa gccaggatcc tcccctaaac ttttgattta taggacatcc atcctggcat | 180 |
| ctggagtcct ggacaccttc agtggcagtg gtctgagag ctcttacact ctgacaatca | 240 |
| gctgcatgca ggacgaagtt gctgccactt actattgtca gcaggggagt agtagcccac | 300 |
| cacacgttcg gagggggac caagctggaa ataaaacggg ctgatgctgc accaactgta | 360 |
| tcca | 364 |

<210> SEQ ID NO 35
<211> LENGTH: 359
<212> TYPE: DNA
<213> ORGANISM: Mus musculus

<400> SEQUENCE: 35

| | |
|---|---|
| gtgccagatg tgagctcgtg atgacccagt ctccagcatc cctgtccgtg gctacaggaa | 60 |
| aaaaagtcac catcagatgc ataagcagca ctgacattga tgatgatatg aactggtacc | 120 |
| agcagaaggc aggaaaacct cctaaactcc ttatttcaga aggcaatatt tttagtcctg | 180 |
| gagtcccatc ccgattctcc agcagtggca atggcacaga ttttgttttt acagttgaaa | 240 |
| acacgctctc agaagatgtt gcagataact actgtttgca aagtgataac atgccattca | 300 |
| cgttcggctc ggggacaaag ttggaataa acgggctga tgctgcacca actgtatcc | 359 |

<210> SEQ ID NO 36
<211> LENGTH: 359
<212> TYPE: DNA
<213> ORGANISM: Mus musculus

<400> SEQUENCE: 36

| | |
|---|---|
| gtgccagatg tgagctcgtg atgacccagt ctccagcatc cctgtccgtg attacaggaa | 60 |
| aaaaagtcac catcagatgc ataagcaaca ctgacattga tgatgatttg aactggtccc | 120 |
| agctgaaggc aggagaacct cctaaactcc ttatttcaga aggcaatatt tttagtcctg | 180 |
| gagtcccatc ccgattctcc agcagtggca atggcacaga ttttgttttt acaattgaaa | 240 |
| acacgctctc agaagatgtt gcaaataact actgtttcca aagtgataac atgccattca | 300 |
| cgttcggctc ggggacaaag ttggaataa acgggctga tgctgcacca actgtatcc | 359 |

<210> SEQ ID NO 37
<211> LENGTH: 19
<212> TYPE: DNA
<213> ORGANISM: Artificial
<220> FEATURE:
<223> OTHER INFORMATION: forward rt-pcr primer for polymerase gene

<400> SEQUENCE: 37

| | |
|---|---|
| cagagccatg cctaacatg | 19 |

<210> SEQ ID NO 38
<211> LENGTH: 20
<212> TYPE: DNA
<213> ORGANISM: Artificial
<220> FEATURE:

<223> OTHER INFORMATION: reverse primer for RT-PCR of polymerase gene

<400> SEQUENCE: 38
aatgtttacg caggtaagcg                     20

<210> SEQ ID NO 39
<211> LENGTH: 18
<212> TYPE: DNA
<213> ORGANISM: Artificial
<220> FEATURE:
<223> OTHER INFORMATION: forward primer for nested PCR of polymerase
      gene

<400> SEQUENCE: 39
tgttaaacca ggtggaac                       18

<210> SEQ ID NO 40
<211> LENGTH: 18
<212> TYPE: DNA
<213> ORGANISM: Artificial
<220> FEATURE:
<223> OTHER INFORMATION: reverse primer for nested pcr of polymerase
      gene

<400> SEQUENCE: 40
cctgtgttgt agattgcg                       18

<210> SEQ ID NO 41
<211> LENGTH: 21
<212> TYPE: DNA
<213> ORGANISM: Artificial
<220> FEATURE:
<223> OTHER INFORMATION: forward primer for real-time pcr of
      nucleoprotein

<400> SEQUENCE: 41
accagaatgg aggacgcaat g                   21

<210> SEQ ID NO 42
<211> LENGTH: 25
<212> TYPE: DNA
<213> ORGANISM: Artificial
<220> FEATURE:
<223> OTHER INFORMATION: reverse primer for real-timer pcr of
      nucleoprotein

<400> SEQUENCE: 42
gctgtgaacc aagacgcagt attat               25

<210> SEQ ID NO 43
<211> LENGTH: 16
<212> TYPE: DNA
<213> ORGANISM: Artificial
<220> FEATURE:
<223> OTHER INFORMATION: TaqMan MGB probe - has 5'
      6-carboxyfluorescein reporter dye

<400> SEQUENCE: 43
accccaaggt ttaccc                         16